US012788629B2

(12) United States Patent
Stowe et al.

(10) Patent No.: US 12,788,629 B2
(45) Date of Patent: Nov. 10, 2026

(54) SYSTEM, METHOD, AND APPARATUS FOR MASSAGING THE EYELID

(71) Applicant: Verily Life Sciences LLC, Dallas, TX (US)

(72) Inventors: Timothy Stowe, Alameda, CA (US); Marty Sheridan, El Granada, CA (US); Gregory B. Arcenio, Redwood City, CA (US)

(73) Assignee: Verily Life Sciences LLC, Dallas, TX (US)

( * ) Notice: Subject to any disclaimer, the term of this patent is extended or adjusted under 35 U.S.C. 154(b) by 698 days.

(21) Appl. No.: 18/216,537

(22) Filed: Jun. 29, 2023

(65) Prior Publication Data

US 2024/0000609 A1 Jan. 4, 2024

Related U.S. Application Data

(60) Provisional application No. 63/356,537, filed on Jun. 29, 2022.

(51) Int. Cl.

| | |
|---|---|
| ***A61F 9/007*** | (2006.01) |
| ***A61H 7/00*** | (2006.01) |
| ***A61N 5/06*** | (2006.01) |

(52) U.S. Cl.

CPC ......... *A61F 9/00718* (2013.01); *A61H 7/004* (2013.01); *A61N 5/0625* (2013.01);
(Continued)

(58) Field of Classification Search

CPC ......... A61B 5/6821; A61B 3/113; A61B 3/14; A61B 3/18; A61B 3/00; A61K 9/0048;
(Continued)

(56) References Cited

U.S. PATENT DOCUMENTS 2,627,752 A * 2/1953 Nicolaus .................. F16B 1/00 74/17.5
3,816,031 A * 6/1974 Joyce, Sr. .............. F02B 75/04 417/364
(Continued)

FOREIGN PATENT DOCUMENTS

CA 2809274 A1 * 3/2012 ............. A61F 7/007
CN 104748045 A * 7/2015 .......... F21V 33/0044
(Continued)

OTHER PUBLICATIONS https://www.giannisarcone.com/wp/reuleaux-triangle-intermittent-mechanisms/ (Year: 2017).*
(Continued)

*Primary Examiner* — Valerie L Woodward
*Assistant Examiner* — Aislinn M Jones
(74) *Attorney, Agent, or Firm* — Christensen O'Connor Johnson Kindness PLLC

(57) ABSTRACT

An apparatus massages an eyelid to move meibum unidirectionally through a meibomian gland duct toward a gland duct orifice at the eyelid margin in order to clear meibum blockage in the gland duct. The apparatus is configured to cyclically apply pressure to an application area of the eyelid, to move the applied pressure in a flow direction toward the gland duct orifice, and release the pressure applied to the application area of the eyelid. The apparatus includes an elongated massage arm configured to support a massage tip, which is configured to apply the pressure to the application area of the eyelid. A cam is rotatable about an axis of rotation and includes a cam surface. A follower includes a follower surface in sliding engagement with the cam surface. The follower is configured to impart massaging motion to the massage arm in response to rotation of the cam. The cam surface has a constant width curve configuration. The cam is
(Continued)

configured so that a center of the cam surface is offset from the axis of rotation of the cam.

20 Claims, 20 Drawing Sheets

(52) U.S. Cl.
CPC .. *A61H 2201/0207* (2013.01); *A61H 2201/10* (2013.01); *A61H 2201/1418* (2013.01); *A61H 2201/1645* (2013.01); *A61H 2201/5082* (2013.01); *A61H 2205/024* (2013.01); *A61N 2005/0652* (2013.01); *A61N 2005/0659* (2013.01)

(58) Field of Classification Search
CPC ............ A61F 2009/0052; A61F 9/0017; A61F 9/009; A61F 9/00; A61F 9/00718; A61N 5/1017; A61N 1/36046; A61N 2005/0652; A61N 2005/0659; A61N 5/0625; A61H 15/02; A61H 2201/0153; A61H 2201/0207; A61H 2201/10; A61H 2201/1418; A61H 2201/1645; A61H 2201/5082; A61H 2205/024; A61H 5/00; A61H 7/003; A61H 7/004; A61H 7/005
See application file for complete search history.

(56) References Cited

U.S. PATENT DOCUMENTS

| | | | | | |
|---|---|---|---|---|---|
| 5,900,923 | A * | 5/1999 | Prendergast | G09B 23/28 351/221 |
| 9,763,827 | B2 * | 9/2017 | Kelleher | A61N 7/00 |
| 2005/0288745 | A1 * | 12/2005 | Andersen | A61F 9/00781 607/86 |
| 2007/0191821 | A1 * | 8/2007 | Boxer Wachler | A61F 9/008 606/9 |
| 2014/0192327 | A1 * | 7/2014 | Sindt | B29D 11/00105 351/200 |
| 2015/0057701 | A1 * | 2/2015 | Kelleher | A61H 23/0245 606/204.15 |
| 2015/0182415 | A1 * | 7/2015 | Olkowski | A61H 23/02 604/295 |
| 2018/0031090 | A1 * | 2/2018 | Wong | F16H 53/02 |
| 2019/0091065 | A1 * | 3/2019 | Kelleher | A61F 9/00802 |
| 2020/0188169 | A1 * | 6/2020 | McMahon | A61F 7/00 |
| 2020/0330270 | A1 * | 10/2020 | Foster | A46B 11/001 |
| 2020/0360723 | A1 * | 11/2020 | Azar | A61H 1/00 |
| 2021/0177650 | A1 * | 6/2021 | Clauson | A61M 35/003 |
| 2022/0145666 | A1 * | 5/2022 | Ma | E05B 55/005 |

FOREIGN PATENT DOCUMENTS

| | | | | | |
|---|---|---|---|---|---|
| CN | 206459903 | U * | 9/2017 | |
| CN | 111195395 | A * | 5/2020 | A61H 15/0078 |
| CN | 112842684 | A | 5/2021 | |
| CN | 113456462 | A * | 10/2021 | A61H 23/02 |
| CN | 113558948 | A * | 10/2021 | A61B 5/0077 |
| DE | 136528 | C | 10/2020 | |
| EP | 0645132 | A1 * | 3/1995 | A61H 23/0254 |
| GB | 2288323 | A * | 10/1995 | A46B 13/02 |
| JP | 2017533074 | A | 11/2017 | |
| JP | 2018094420 | A * | 6/2018 | B65D 47/18 |
| KR | 20200099677 | A * | 8/2020 | A61N 5/0616 |
| WO | WO-0053145 | A1 * | 9/2000 | A61H 23/04 |
| WO | WO-2009122556 | A1 * | 10/2009 | A61H 1/005 |
| WO | WO-2014159696 | A1 * | 10/2014 | A61L 2/28 |
| WO | WO-2014179356 | A1 * | 11/2014 | A61F 9/00718 |
| WO | WO-2018098419 | A1 * | 5/2018 | A61N 5/062 |
| WO | WO-2018153368 | A1 * | 8/2018 | G06F 3/013 |
| WO | WO-2019033415 | A1 * | 2/2019 | G02C 7/10 |
| WO | WO-2020215084 | A1 * | 10/2020 | A61F 9/00709 |
| WO | 2020232217 | A1 | 11/2020 | |
| WO | WO-2022065785 | A1 * | 3/2022 | A61H 15/0078 |

OTHER PUBLICATIONS

Sarcone, G. (Nov. 12, 2017). Reuleaux-triangle intermittent mechanisms. Sarconista. https://www.giannisarcone.com/wp/reuleaux-triangle-intermittent-mechanisms/ (Year: 2017).*

International Searching Authority, International Search Report and Written Opinion of the International Searching Authority, International Application No. PCTUS2023/026645, mld Oct. 27, 2023, 11 pages, ISA/EPO, Netherlands.

Japan Patent Office, Notice of Reasons for Refusal, Application No. 2024-574681, mld Feb. 20, 2026, 5 pages.

European Patent Office, Communication pursuant to Article 94(3) EPC, Application No. 23 749 195.6, mld Feb. 2, 2026, 11 pages, Munich, Germany.

* cited by examiner

| Cam Position | Arm Position | Tip Linear Position (Left/Right) | Tip Pivot Position (Up/Down) |
|---|---|---|---|
| 0° |  | 0 mm (Center) | +1.0 mm (Up) |
| 45° |  | -0.5 mm (Left) | +1.0 mm (Up) |
| 90° |  | -0.5 mm (Left) | -1.0 mm (Down) |
| 135° |  | -0.5 mm (Left) | -1.0 mm (Down) |
| 180° |  | 0 mm (Center) | -1.0 mm (Down) |
| 225° |  | +0.5 mm (Right) | -1.0 mm (Down) |
| 270° |  | +0.5 mm (Right) | +1.0 mm (Up) |
| 315° |  | +0.5 mm (Right) | +1.0 mm (Up) |

SYSTEM, METHOD, AND APPARATUS FOR MASSAGING THE EYELID

CROSS REFERENCE TO RELATED APPLICATIONS

This application claims the benefit and priority of U.S. Provisional Application No. 63/356,537, filed on Jun. 29, 2022, the entire disclosure of which is incorporated herein by reference in its entirety.

TECHNICAL FIELD

This disclosure relates to a system, method, and apparatus for massaging the eyelid.

BACKGROUND

The ocular surface of the eye is coated with a three-layer film commonly referred to as a tear film or tears. As shown in FIGS. 1 and 2, the three layers of tear film are a mucin layer, which adheres to the ocular surface (epithelium), a middle aqueous layer, and an upper/outer lipid meibum layer. The mucin and aqueous layers are produced by the lacrimal gland and other glands within the conjunctiva of the eye. The meibum layer is produced by meibomian glands in the eyelid. Tears flow from the ocular surface through the nasolacrimal canal, which drains into the back of the nose and throat.

The mucin layer of the tear film is hydrophilic, which helps spread the aqueous layer evenly over the ocular surface. Together, the mucin and aqueous layers aid in maintaining the lubrication across the ocular surface and reducing shear stress during blinking or rubbing. Meibum forms the top layer of the tear film. Being primarily a lipid in composition, the meibum layer has lower surface tension and forms an outer film that lowers the rate of aqueous evaporation. This keeps the aqueous layer more uniform and free of dry spots, thereby lubricating the ocular surface for a longer period of time without needing to be refreshed. Tear film is anti-microbial and helps maintain the health of the eye, as well as clear any contaminants or particles that might come into contact with the eye.

Dry eye disease, or DED, affects millions of people worldwide. According to some studies, the third most common reason for visiting an ophthalmologist's office is for dry eye disease symptoms. Recently it has been shown that up to 80% of dry eye cases also have a component called meibomian gland dysfunction or MGD. Normally, the lipid layer produced by the meibomian glands spreads evenly into a thin (approximately 200 nm thick) protective film over the air-tear interface above the cornea.

Every time the eye blinks, a slight amount of the meibomian lipid protective film is spread. However, there are many conditions under which not enough meibomian spreads out over the aqueous tear film. Root causes can include but are not limited to hormonal changes in the meibomian oil production that effect properties such as viscosity, capped glands at the eyelid margin, skin mites living in the eyelashes, prolonged infection such as difficult to remove styes, general inflammation (Blepharitis), autoimmune diseases or allergic reactions, and more recently the inadequate blinking from excessive screen time known as computer vision syndrome (CVS).

The absence of an adequate outer protective lipid layer reduces the evaporation time for the tear film covering the eye, leading to the possibility of dry spots over the cornea epithelium. This is measured quantitatively as the so-called tear film break-up time metric abbreviated as TBUT or TFBUT.

In the past, mild MGD has been addressed by using warm compresses, eyelid cleansing compounds, and massaging the eyelids gently. These approaches, however, have not been shown to clinically be effective in the majority of severe dry eye cases.

More recent treatments involve heating up the meibomian glands from inside the eyelids to melt or soften the oils which have become clogged. As the eyelids are heated from the inside, heat is delivered directly to the meibomian gland. In some instances, air bladders are also used to massage the meibomian glands to help express the softening oil clogs from the glands. However, such procedures can still be highly invasive and costly procedures requiring an expert ophthalmologist and multiple treatments each year. Other known eye treatments include heating the outside of the eyelids using heating pads. In this type of procedure, ophthalmologists must still use forceps with an intermediate pressure to effectively express the glands. Such treatments are also invasive and can be uncomfortable for the patient.

SUMMARY

A system, method, and apparatus is configured to treat MGD by massaging an eyelid or eyelids to move meibum unidirectionally through a meibomian gland toward the meibomian gland orifice at the eyelid margin. The system, method, and apparatus can additionally be configured to heat the meibomian glands while massaging the eyelid. The system, method, and apparatus implements an eye shield that at least partially covers the eyeball in order to protect the eye and to help fix the position of the apparatus relative to the eye. Retractable massage arms have soft massage tips that engage the eyelids and apply a massage motion to express the meibum from the meibomian gland through the gland orifice.

Through the motion imparted by the massage arms, the massage tips apply the massage treatment in a rectangular motion according to the following sequence of motions, which is repeated throughout the treatment session:

- The massage tip moves linearly toward the eyelid and engages with the eyelid surface under pressure.
- The massage tip pivots downward (in the case of massaging the upper eyelid) or upward (in the case of massaging the lower eyelid) to express the meibum from the meibomian gland expressing meibum towards the exit gland orifice.
- The massage tip moves linearly away from the eye (i.e., retracts) out of engagement with the eyelid.
- The massage tip pivots upward (in the case of the upper eyelid) or downward (in the case of the lower eyelid), while disengaged, back to the starting position.

The motion of the massage tips is imparted by the massage arms through a cam/follower mechanism configured to translate the rotational motion imparted by a drivetrain to the sequence of movements of the massage arms outlined above. The cam has a rounded polygonal configuration with a cam surface that forms a curve of constant width, similar to a Reuleaux triangle. The follower has a square configuration with a square follower surface having a width about equal to the width of the constant curve of the cam. The cam thus fits within the follower and can rotate within the follower, with the cam surface maintaining a constant engagement with the follower surface. The rotational axis of the cam is offset from its center so as to produce an eccentric motion when rotated. Through this eccentric motion, in combination with the respective configurations of the cam and follower, the massage tip motion is produced.

According to one aspect, An apparatus massages an eyelid to move meibum unidirectionally through a meibomian gland duct toward a gland duct orifice at the eyelid margin in order to clear meibum blockage in the gland duct. The apparatus is configured to cyclically apply pressure to an application area of the eyelid, to move the applied pressure in a flow direction toward the gland duct orifice, and release the pressure applied to the application area of the eyelid. The apparatus includes an elongated massage arm configured to support a massage tip, which is configured to apply the pressure to the application area of the eyelid. A cam is rotatable about an axis of rotation and includes a cam surface. A follower includes a follower surface in sliding engagement with the cam surface. The follower is configured to impart massaging motion to the massage arm in response to rotation of the cam. The cam surface has a constant width curve configuration. The cam is configured so that a center of the cam surface is offset from the axis of rotation of the cam.

According to another aspect, the cam and the follower can be configured so that the massaging motion follows a rectangular path.

According to another aspect, the rectangular path can be configured sequentially to be axially toward the eyelid into engagement with the application area, linearly along the eyelid in the flow direction of the meibomian gland duct while engaged with the application area, axially away from the eyelid to disengage from the application area, and linearly in a direction opposite the flow direction while disengaged from the application area.

According to another aspect, the cam and the follower can be configured so that the massaging motion of the massaging comprises the following movements in a repeating cycle:

- a first movement comprising moving from an initial position into engagement with and applying pressure to the application area of the eyelid;
- a second movement comprising moving in the flow direction toward the gland duct orifice while applying pressure to the application area;
- a third movement comprising moving away and disengaging from the eyelid; and
- a fourth movement comprising returning to the initial position.

According to another aspect, the follower surface can be a surface of the massage arm.

According to another aspect, follower can include an opening in the massage arm, and the cam can be positioned in the opening. The opening can have a width greater than a width of the constant width curve of the cam surface. The width of the opening can be configured to allow the cam to rotate within the opening while engaging the follower surface.

According to another aspect, the opening can have a generally square shape.

According to another aspect, the cam can be configured so that the cam surface is maintained in constant contact with all four sides of the square opening of the follower.

According to another aspect, the apparatus can also include a pin/slot mechanism that supports the massage arm on the housing. The pin/slot mechanism can include a fixed pin supported on the housing and a slot on the massage arm through which the pin extends. The massage arm can be configured to pivot about the fixed pin and to slide on the fixed pin along the length of the slot.

According to another aspect, the cam and follower can be configured so that rotational motion of the cam produces a rectangular motion of the massage tip.

According to another aspect, the apparatus can also include at least one source of infrared light configured to heat the meibum in the eyelid meibomian gland ducts through the massage tip, either independently from the massage motion of the massage tip or simultaneously with the motion of the massage tips.

According to another aspect, the infrared light can be emitted at a wavelength of about 900 nm to 1100 nm, preferably at a wavelength of about 985 nm to 1015 nm.

According to another aspect, the apparatus can also include an eye shield configured to engage and cover at least a portion of the eye and to be positioned between the eye and the eyelid to shield the eye from the infrared light.

According to another aspect, the eye shield can also include at least one temperature sensor configured to sense the temperature in the area of the eye and eyelids exposed to the infrared light.

According to another aspect, the eye shield can include a translucent portion through which visible can pass. The translucent portion can be configured to allow for a camera to image the eyelids during treatment.

According to another aspect, the massage tip can be configured to allow infrared radiation to pass through and apply heat to the eyelid.

According to another aspect, the apparatus can also include latching arms with latching tips configured to move toward each other to a latching condition in which the latching tips latch a tab portion of the eye shield to secure the eye shield to the apparatus and constrain movement of the eye shield relative to the massage arms.

According to another aspect, the apparatus can also include a treatment arm that is actuatable from a retracted position to an treatment position. The treatment arm can be configured to move the latching arms to the latching condition when in the treatment position. The treatment arm can also be configured to move the latching arms to the release condition when in the retracted position. The treatment arm also includes a spring member configured to bias the treatment arm to the retracted condition when released so that a quick-release of the eye shield tab portion is effectuated automatically.

According to another aspect, the treatment lever can also be configured to control actuation of a forward positioning carriage that carries the massage arms. The treatment lever can be configured to move the forward positioning carriage linearly to position the massage arms in a retracted condition when not applying massage motion, and an extended position for applying massage motion to the eyelids.

According to another aspect, the apparatus can also include an LED array arranged to provide light for optical heating. The LED array can be configured for adjustment in brightness to provide high contrast imaging light for video imaging of the meibomian glands for a brief period during heating.

According to another aspect, the LED heating array can be is supported on a PCBA connected to a heat sink. The PCBA can also support mounting of a micro camera.

According to another aspect, the eye shield also includes a transparent portion that includes one or more embedded mirror surfaces. The mirror surfaces can be configured to allow the micro camera to view the eyelid and meibomian gland duct orifices edge-on by redirection the chief collection rays of the micro cameras towards the upper and lower eyelid margins.

According to another aspect, the apparatus can also include a fan and a heatsink for cooling the LED array.

According to another aspect, the apparatus can also include a magnetic sensor linked electronically to a kill switch for turning off the LED array in response to release of the treatment arm. The magnetic sensor can activate the kill switch by sensing the proximity of one or more magnets mounted on the treatment arm.

According to another aspect, the cyclically applied pressure can be configured to be 8 psi or less.

DRAWINGS

The invention is illustrated by way of example and not limitation in the accompanying drawing figures, in which.

DESCRIPTION

A system, method, and apparatus is configured to treat MGD by massaging one or both eyelid(s) to move meibum unidirectionally through a meibomian gland toward the meibomian gland orifice at the eyelid margin. The system, method, and apparatus can additionally be configured to heat the meibomian glands while massaging the eyelid. An example configuration of an MGD treatment system 10 including an MGD treatment apparatus 20 configured to implement the method for treating MGD is illustrated in FIGS. 3-25.

Figure 1:
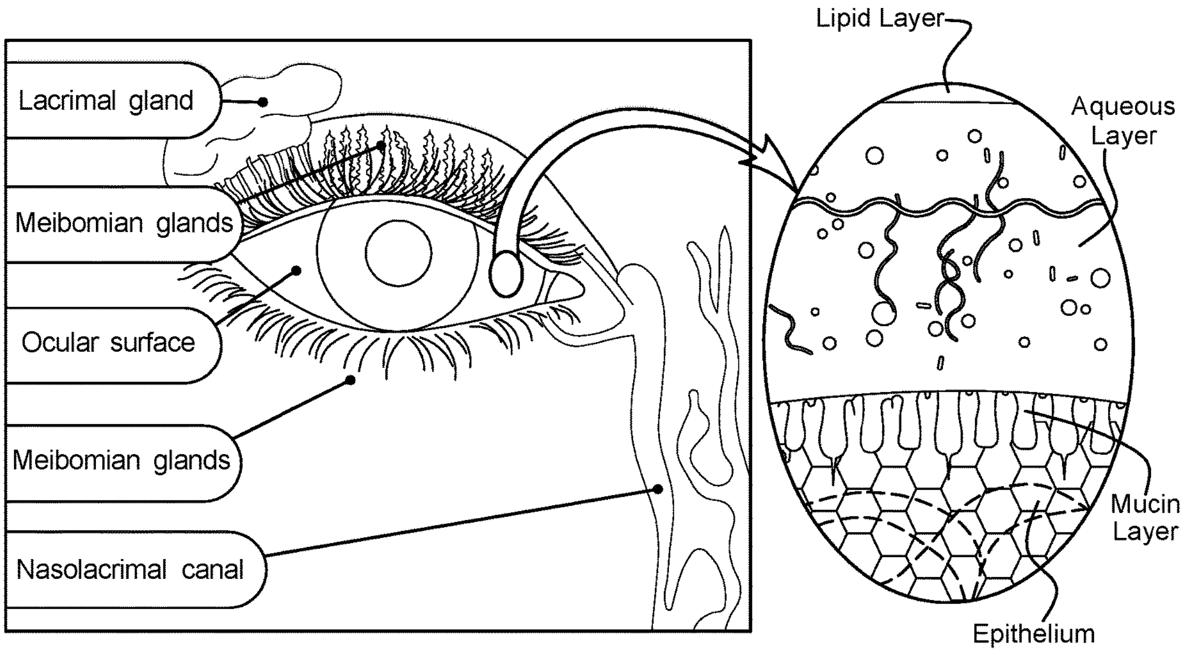
FIG. 1 illustrates certain anatomical features of a subject in the area of the eye, and the various layers of a tear film that coats the surface of the eye.
Figure 2:
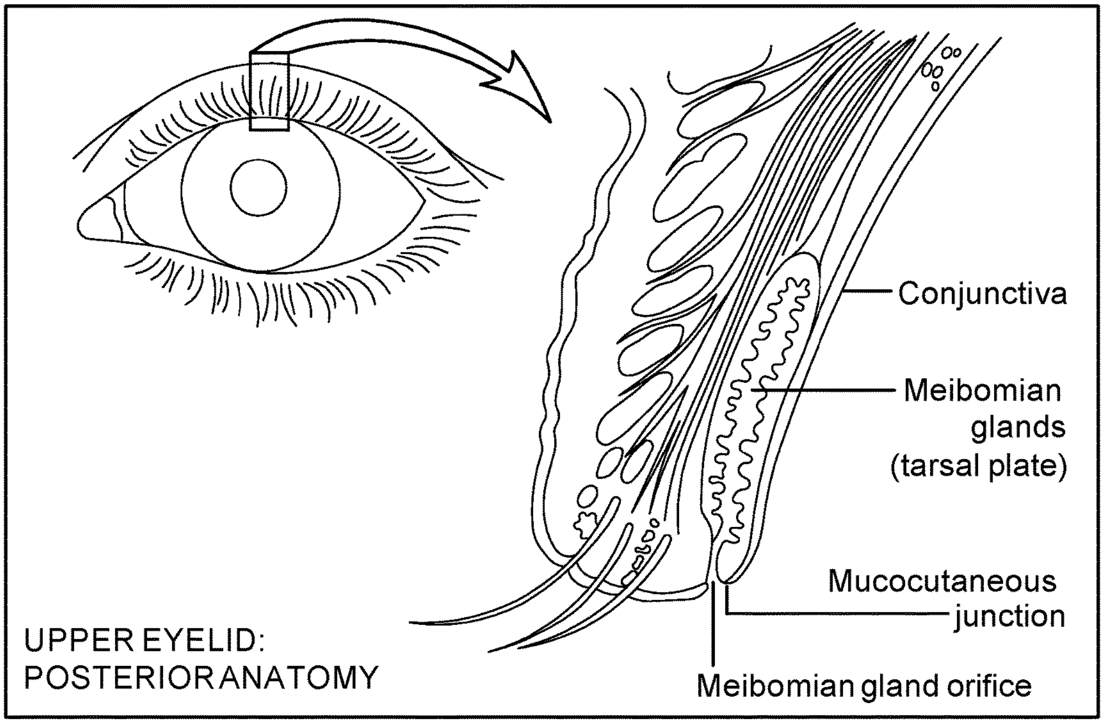
FIG. 2 illustrates certain anatomical features of an eyelid of the subject.
Figure 3:
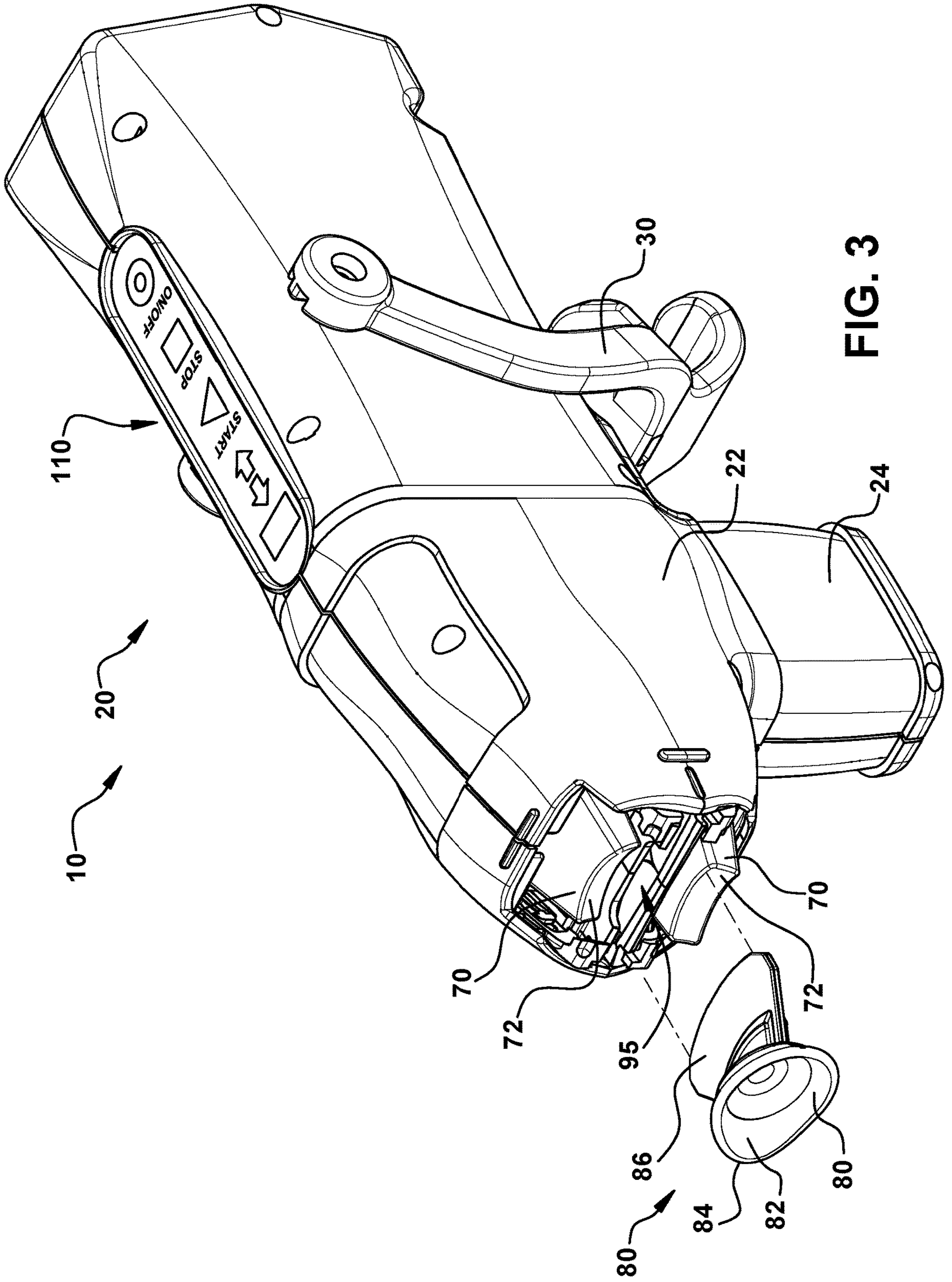
FIG. 3 is a front/top perspective view illustrating an apparatus that forms at least a part of a system that implements a method for treating MGD.
Figure 4:
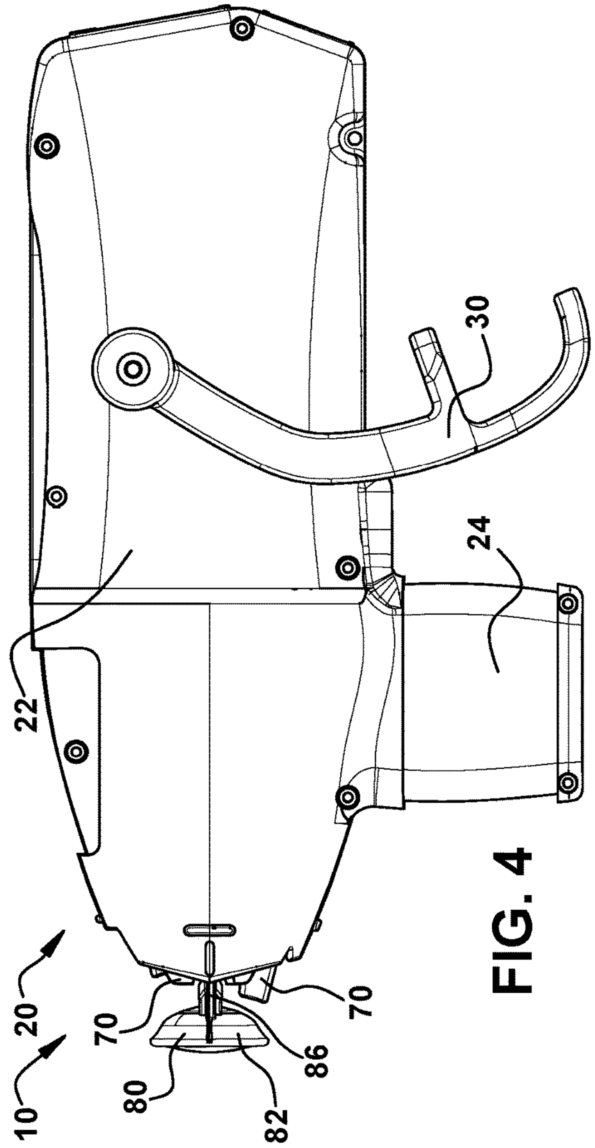
FIG. 4 is a side view of the apparatus in a first condition.
Figure 5:
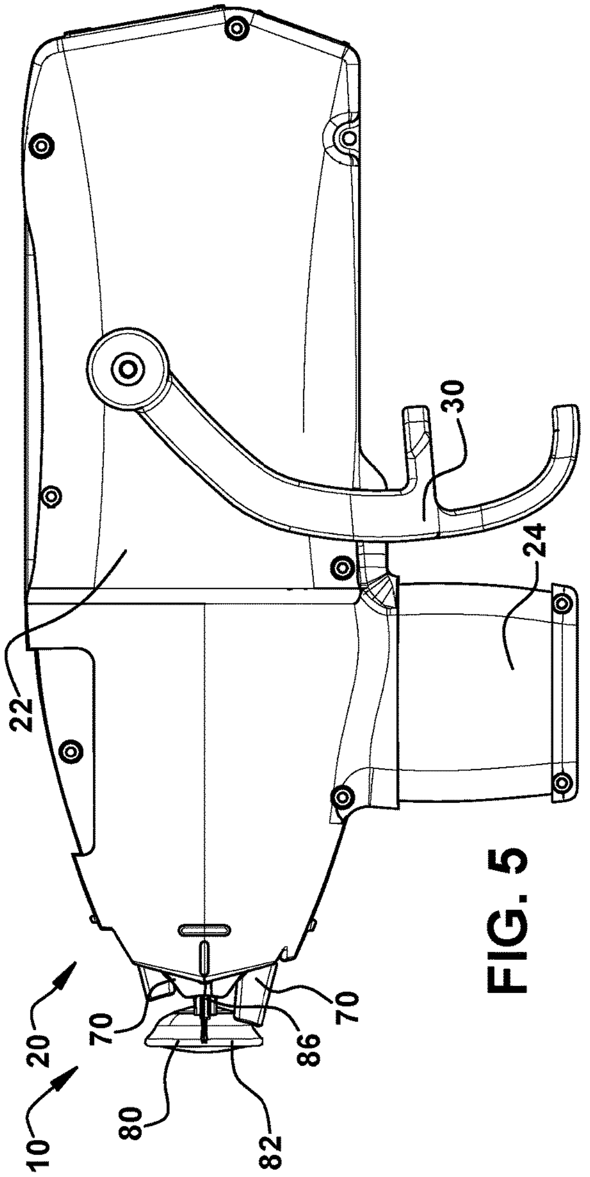
FIG. 5 is a side view of the apparatus in a second condition.
Figure 8:
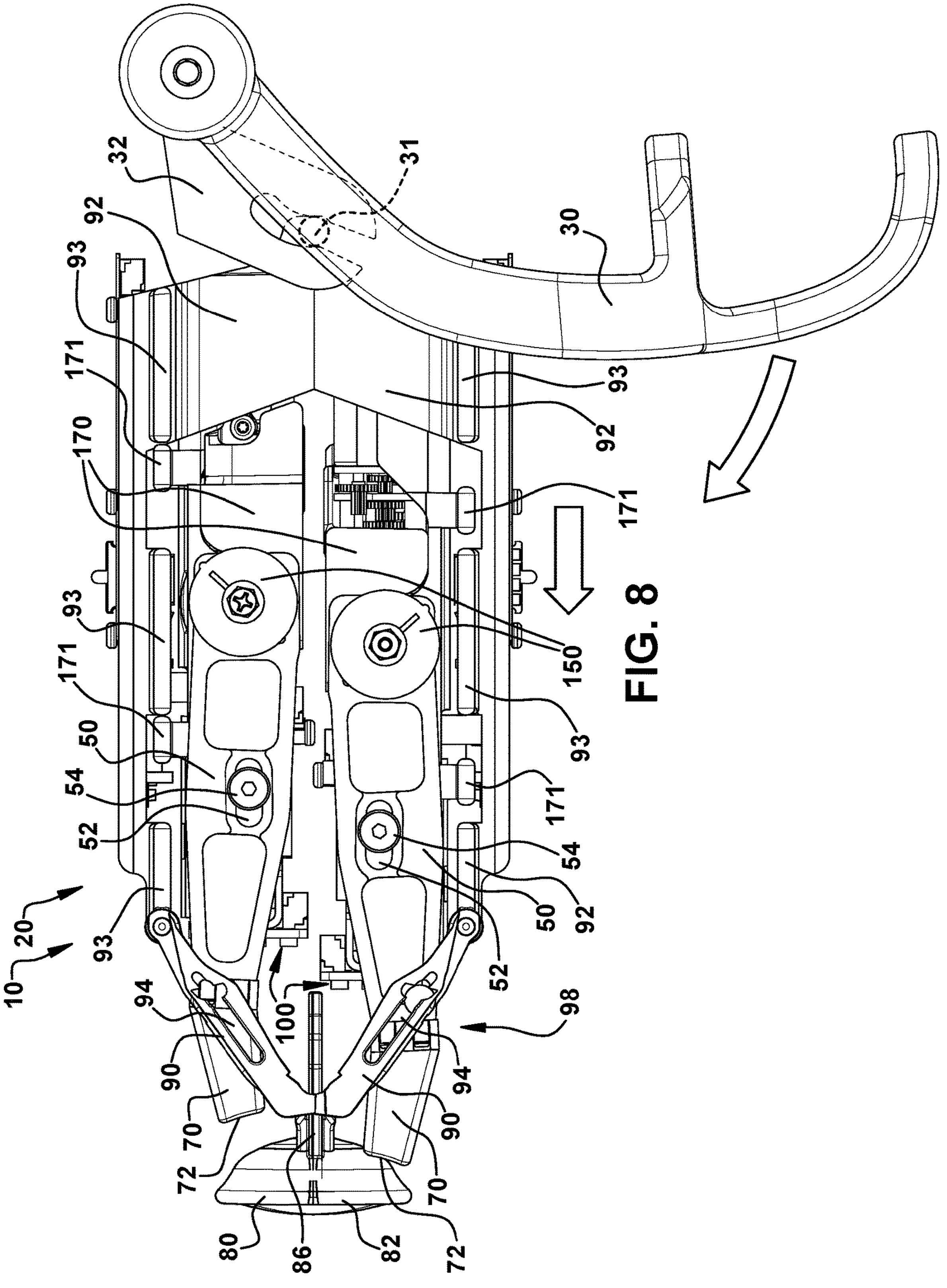
FIG. 8 is a side view illustrating certain components of the apparatus corresponding to the second condition of the apparatus shown in FIG. 5.
Figure 11:
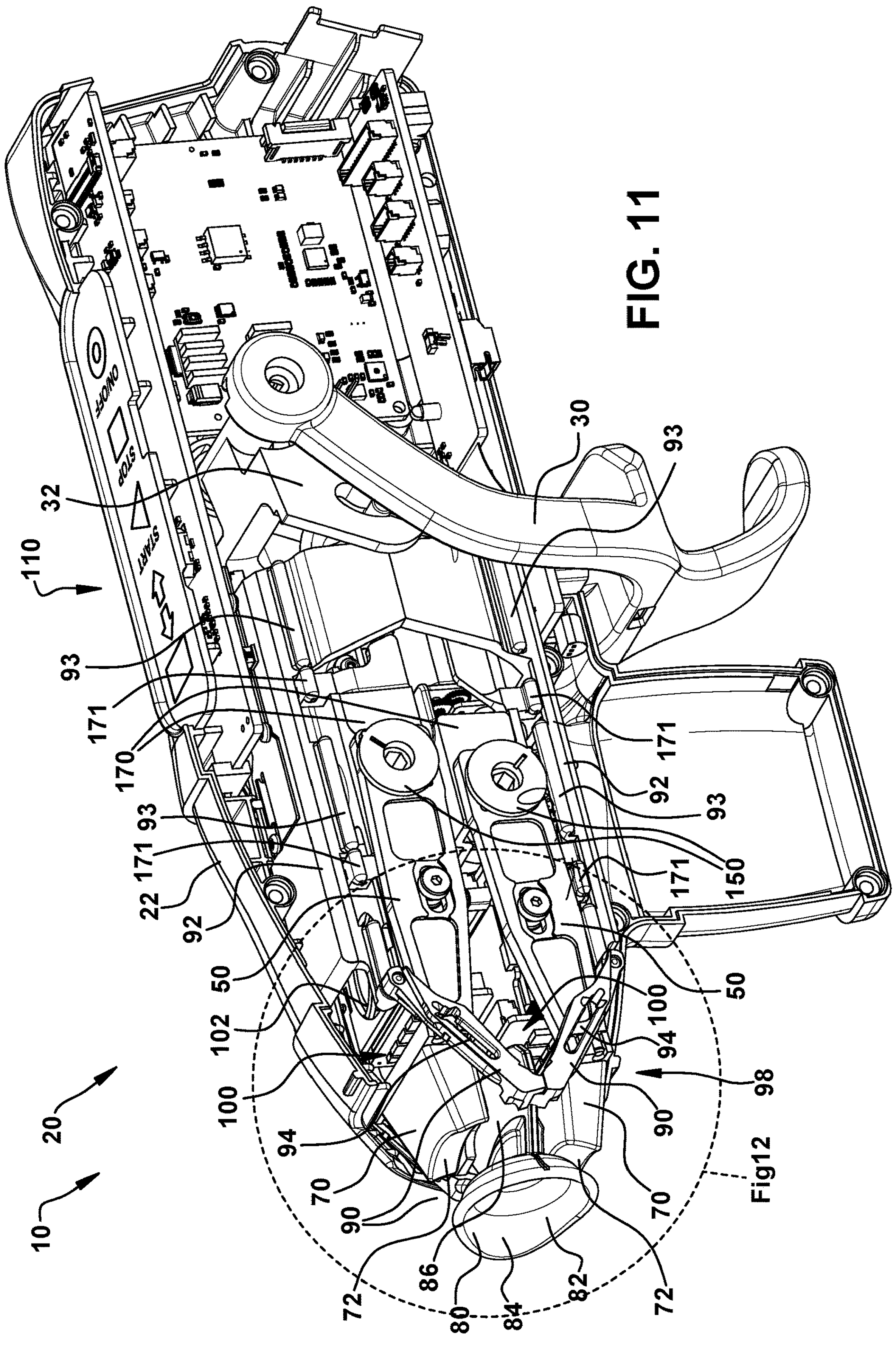
FIG. 11 is a front/top perspective view with a partial cutaway revealing internal components of the apparatus in the second condition of FIG. 5.

The apparatus 20 includes a housing 22 that supports the components described herein. A battery pack 24 supplies the electricity for operating the apparatus 20. As shown, for example, in FIGS. 4, 5, 6-8, and 11, a treatment lever 30 is operable to actuate the apparatus from a retracted condition (FIGS. 4, 6, 7) to an extended condition (FIGS. 5, 8, 11). The retracted and extended conditions of the apparatus 20 refer to the conditions of massage arms 50 (FIG. 6) through which a massaging motion is applied to the eyelids via massage tips 70 that are attached to ends of the massage arms. In the configuration illustrated in the figures, the apparatus 20 includes upper and lower massage arms that, through their associated massage tips 70, can massage the upper and lower eyelids (see FIG. 16) of the subject experiencing MGD. As shown, the apparatus 20 can be compact in form in order to promote ease of use. The apparatus can, for example, be no larger and weigh less than a similarly shaped handheld camcorder used by videographers.

The apparatus 20 also includes an eye shield 80 that serves several purposes. First, the eye shield 80 shields the interior of the eye including the retina and cornea from infrared (IR) light applied to the via an array of light emitting diodes (LEDs), referred to herein as an LED array 100. The LED array 100 is mounted on a printed circuit board assembly (PCBA) 101, which is integrated in the apparatus 20. The LED array 100 is configured to heat the eyelids in order to soften and/or loosen clogged meibomian glands to improve meibum flow. Any excess heat that reaches the eyecup 82 eyecup, which is placed inside the eyelids, is reflected back towards the meibomian glands. Second, the eye shields 80 help to coordinate the relative position the apparatus 20 to the eye/eyelids and maintain that relative position throughout the therapy session. Lastly, the eye shields 80 prevent any squeezing pressure during milking motion on the eyelids from transferring to the eyeball orbital inside the eye socket.

The eye shield 80 is easily attached/detached from the apparatus 20, which allows the eye shield 80 to be applied to the eye while detached. With the eye shield 80 in place on the eye, it can be connected to the apparatus 20 via a quick-release mechanism, which is described in detail below. Once the eye shield 80 is installed, the apparatus 20 is placed in the extended position via the treatment lever 30 for therapy.

Figure 10A:
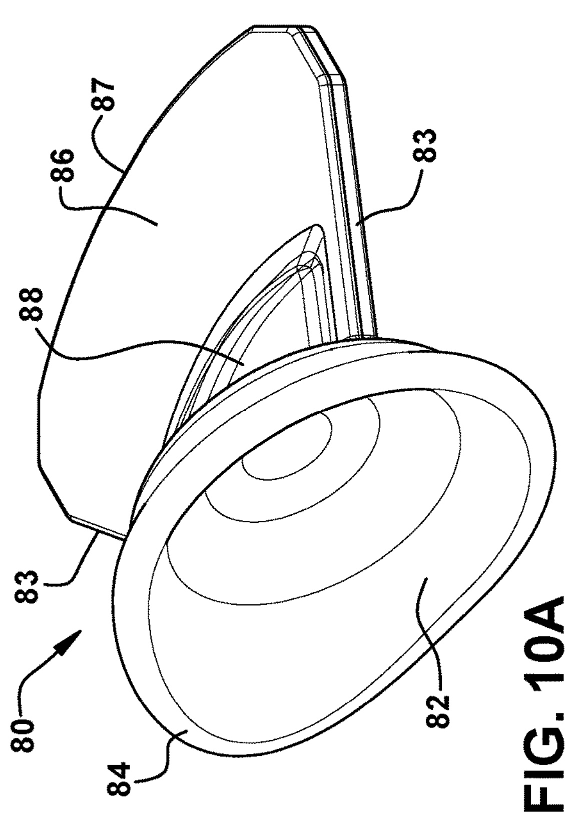
FIGS. 10A and 10B are front-top and rear-top perspective views of a portion of the apparatus.
Figure 10B:
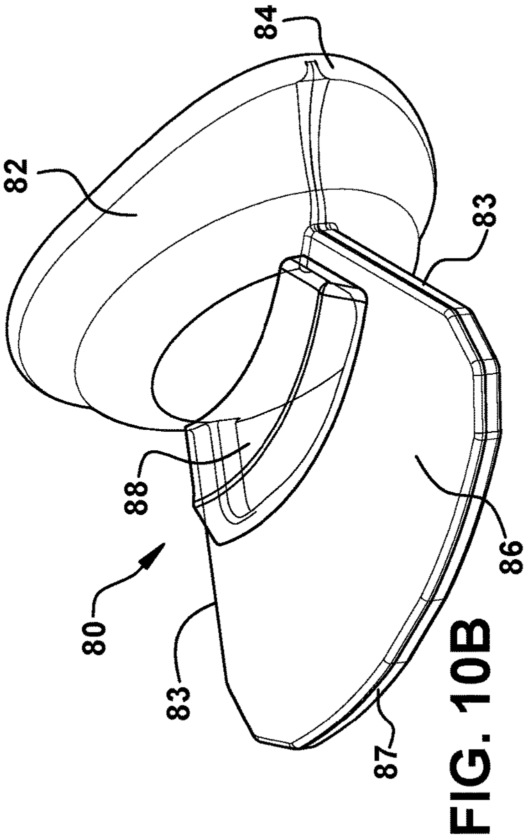
Figure 9:
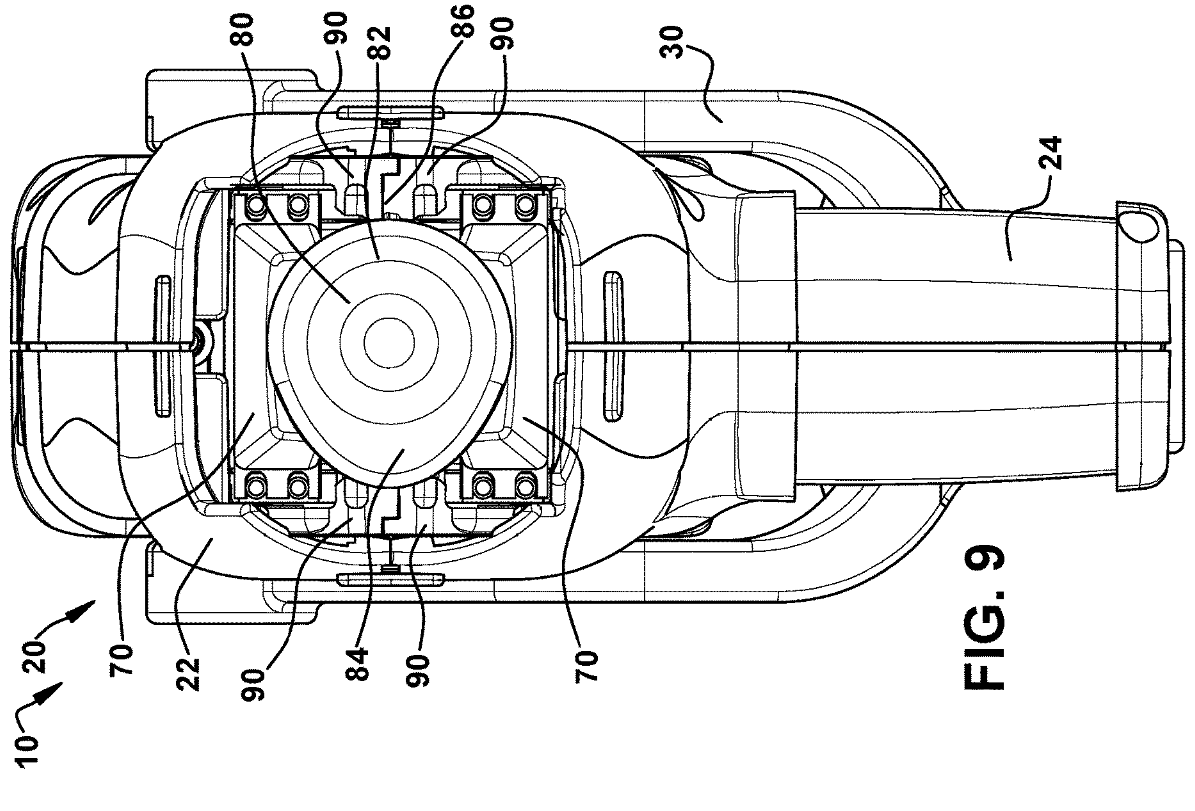
FIG. 9 is a front view of the apparatus.
Figure 16:
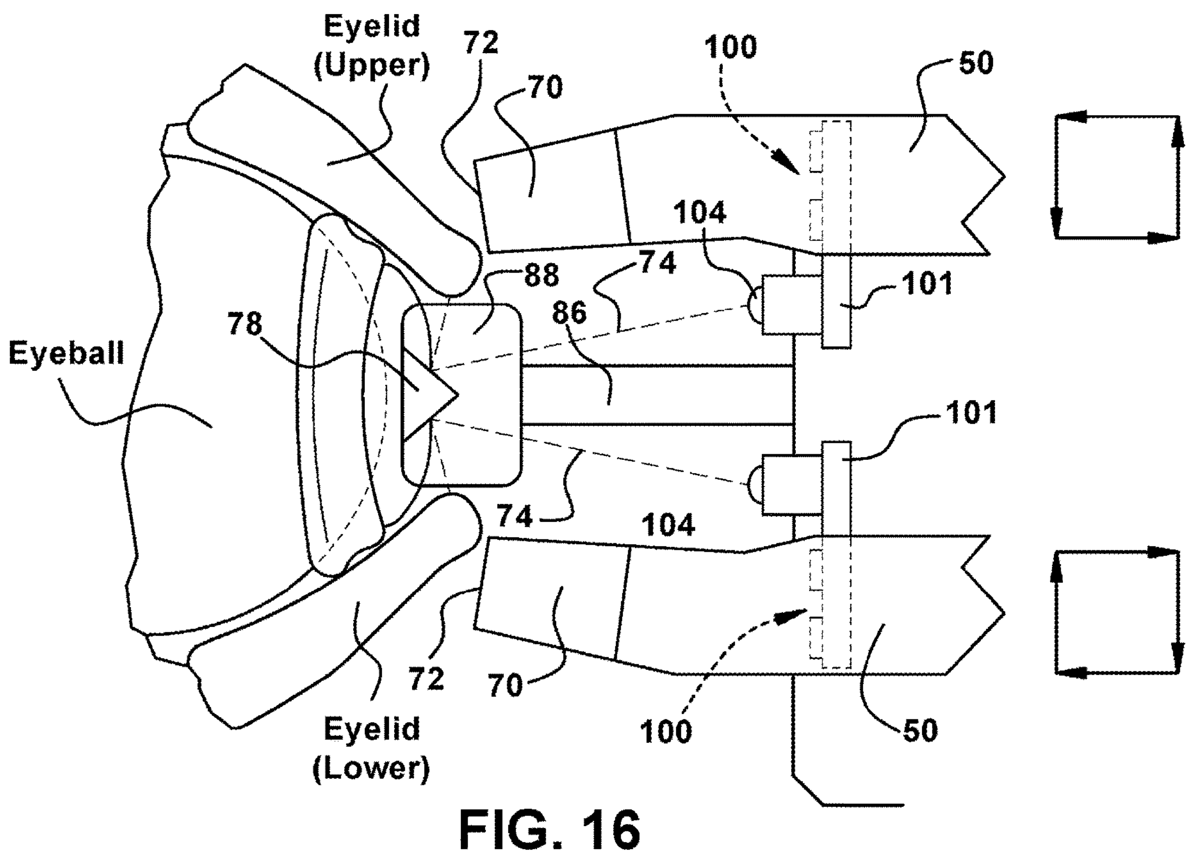
FIG. 16 is a schematic illustration depicting the manner in which components of FIGS. 13-14 apply treatment to a patient.

The eye shield 80 is shown in detail in FIGS. 10A and 10B. As shown, the eye shield 80 includes an scleral shaped eyecup 82 configured to be positioned slightly above the surface of the cornea in a manner similar or identical to that of a hard contact lens (FIG. 16). The shape of the eyecup 82 can be spherical or parabolic and can include flaring 84 at the temporal or nasal edge for enhanced coverage and protection. The eyecup 82 is constructed of a biocompatible material that reflects IR light in order to protect the eye. The eyecup 82 can, for example, be constructed of a Poly(methyl methacrylate) or "PMMA" material.

The eye shield 80 also includes an integrated structure in the form of a tab 86 for supporting the eyecup 82 and making it much easier to place in or take out of the eye. The eye shield tab 86 is configured to be latched onto by a quick-release mechanism 98 that includes latching arms 90 with latching tips 108 configured to capture the eye shield 80 by latching around the angled edges of eye shield tab 86. The latching arms 90 are supported within the housing 22 on a forward positioning carriage 92 to which they are connected. Specifically, ends 106 (see FIG. 12) opposite the capturing tips 108 of the latching arms are pivotally connected to the forward positioning carriage 92. Between the ends 106 and the latching tips 108, the latching arms 90 include slots 94 that receive a stationary pin (not shown) so that the latching arms can slide along the pin and pivot relative to the pin.

Forward movement of the forward positioning carriage 92 causes the latching tips 108 to simultaneously move forward, out of the housing 22 and toward each other. Conversely, rearward movement of the forward positioning carriage 92 causes the latching tips 108 to simultaneously move away from each other and retract into the housing 22. The quick-release mechanism 98 is configured to be operated through actuation of the treatment lever 30, which causes sliding forward/rearward movement of the forward positioning carriage 92.

Figure 6:
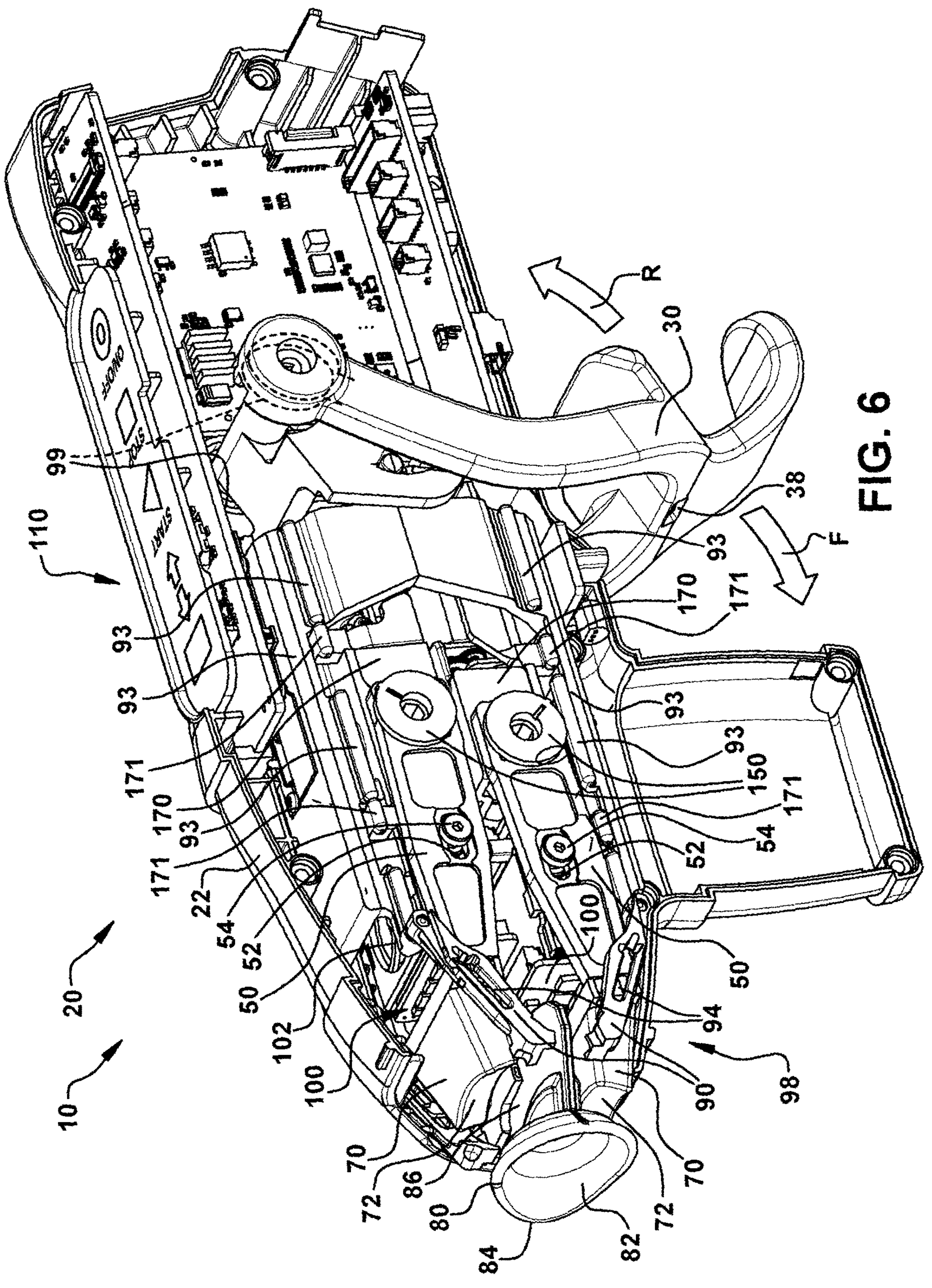
FIG. 6 is a front/top perspective view with a partial cutaway revealing internal components of the apparatus in the first condition of FIG. 4.
Figure 7:
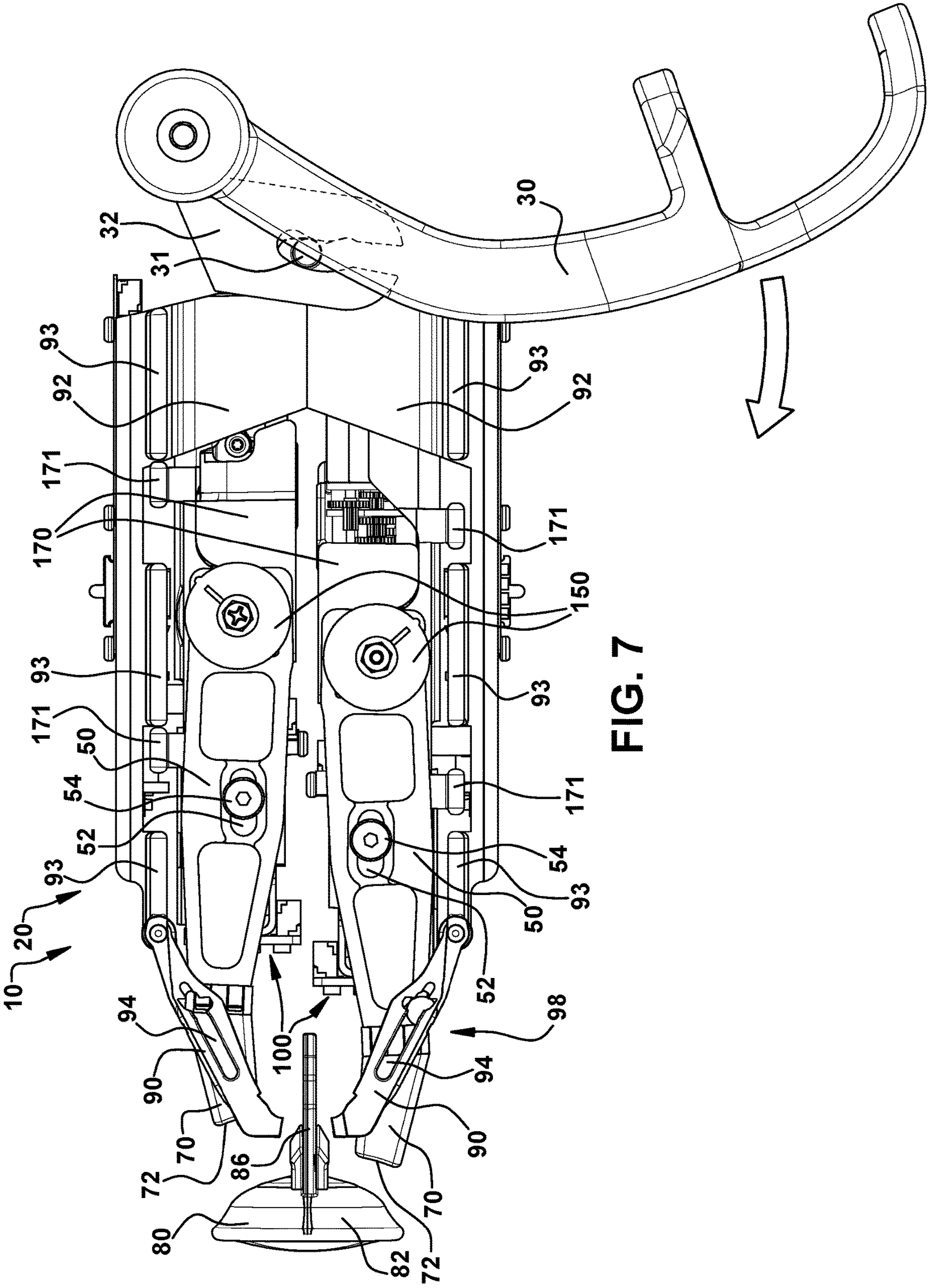
FIG. 7 is a side view illustrating certain components of the apparatus corresponding to the first condition of the apparatus shown in FIG. 4.

In the forward locking position of the treatment lever 30 indicated generally by the arrow F in FIG. 6, the quick-release latching arms 90 capture the eye shield tab 86 of the eye shield along outside angled edges of the eye shield tab 86. In the rearward, release position of the treatment lever 30 indicated generally by the arrow R in FIG. 6, the quick-release mechanism latching arms 90 slide back along 92 thus opening up along the edges of eye shield tab 86 releasing the eyecup 80 from the handheld treatment device 20. Torsion springs 99 bias the treatment lever 30 toward the retracted position, so that a quick-release of the eye shield 80 occurs automatically and quickly in response to releasing the treatment lever 30.

To facilitate the capturing function of the eye shield and to the ensure a quick-release of the eyecup 80, tips 108 of the latching arms 90 have an interlocking interface with each other, with keyed surfaces 96 (see FIG. 12) that reach over the outside edges of the eye shield tab 86. In addition, a horizontal receiving slot 95 (see FIG. 3) constrains the eye shield tab 86 in the vertical direction once the tips 108 of the latching arms 90 are interlocked. Conversely, placing the treatment lever 30 in the rearward position effectuates a quick-release of the eyecup 80 by pulling apart the latching arms 90. Thus, as soon as the treatment lever 30 moves rearward toward the release position, the resulting movement of the keyed surfaces 96 away from each other causes the immediate release of the eye shield tab 86. As mentioned above, the torsion springs 99 ensure that the treatment lever 30 moves rearward as soon as it is released by the user.

Figure 12:
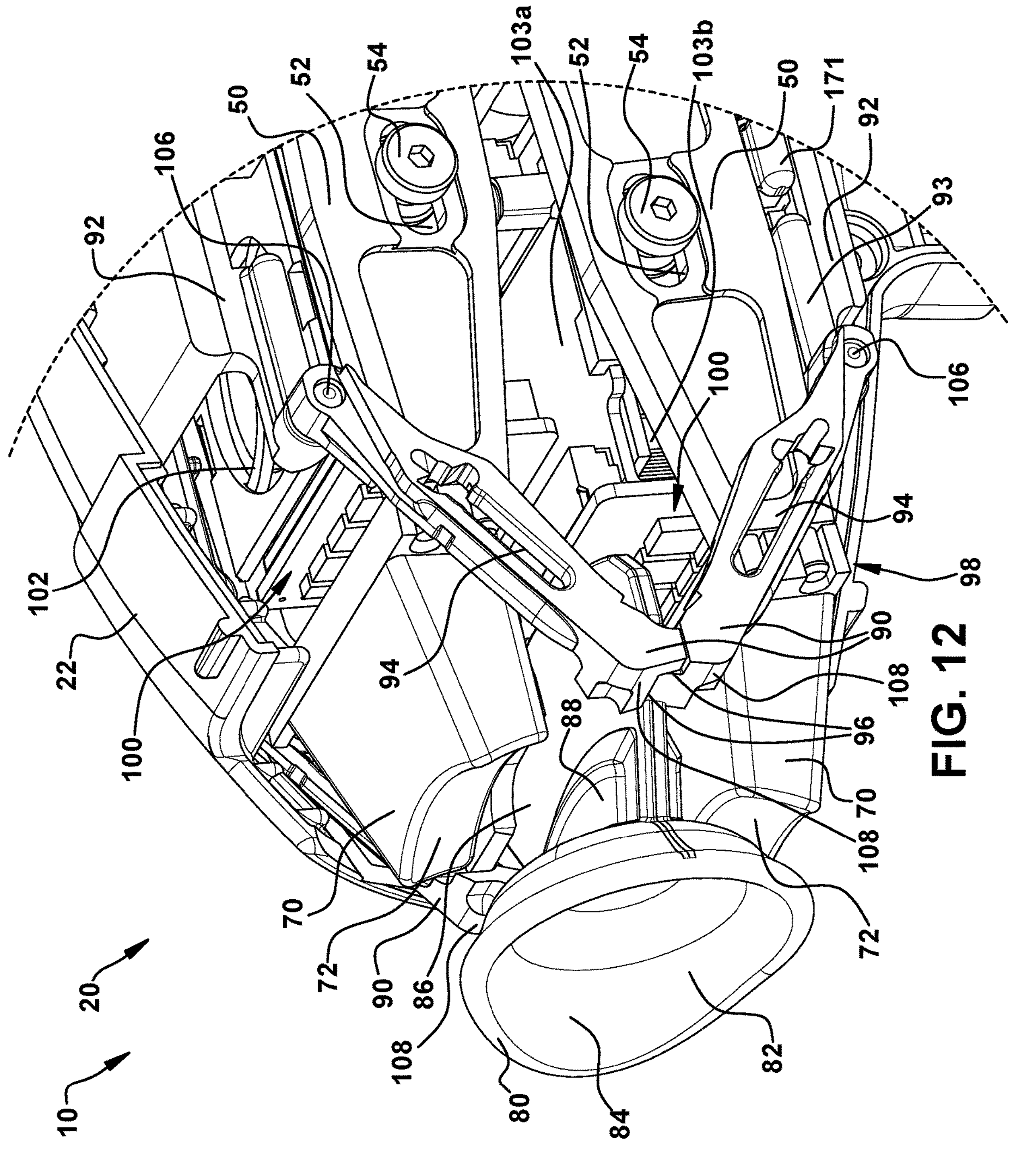
FIG. 12 is a magnified view illustrating the components of the apparatus in the circled portion of FIG. 11.

When the latching arms 90 are in the condition of FIG. 12, the eye shield tab 86 is captured by the latching arms as shown in FIG. 26. In this condition, the angled surfaces 83 of the eye shield tab 86 are is constrained by complimentary surfaces 85 on the tips 108 of the latching arms 90. A rear edge 87 of the eye shield tab 86 is constrained by a complimentary surface 89 on the housing 22. As mentioned previously, up and down motion of the eye shield tab 86 is constrained by complimentary surfaces of the housing 22 that define the slot 95 (see FIG. 3). By "constrained," it is meant to represent the fact that the connection of the eye shield tab 86 to the apparatus 20 is not rigid. Instead, the tab 86 is constrained so that some freedom of movement of the eye shield 80 relative to the remainder of the apparatus 20 is permitted. This freedom of movement accounts for slight movements of the apparatus 20 when being held by the doctor during use.

Supported on the massage apparatus 20, the eyecup 82 is presented in the forward facing manner shown in the figures. The eye shield tab 86 can also include an internal, thin, near-field communication radio frequency identification (NFC RFID) flex circuit that can wirelessly authenticate the eye shield as well as communicate the temperature of temperature sensors embedded in the top and bottom portions of the eyecup during treatment. The wireless technology is similar to that used for wireless credit card payment transactions. The eye shield tab 86 can be constructed of a plastic medical-grade overcoating for biocompatibility. Finally, an optional transparent insert 88 can be provided to allow for real time viewing of the eyelids margins and meibomian gland expression during treatment via integrated IR micro cameras mounted on the PCBA 101.

The eye shield tab 86 is captured by the outside latching arms so as to be supported relative to the housing 22 and internal massage supporting structure known as massage carriages 170. The apparatus 20 includes two massage carriages 170, one associated with each (upper and lower) of the massage arms 50. In this manner, the massage arms 50 and the massage tips 70 move relative to both the housing 22 and the eye shield 80 and can be fine-tunes, as described herein, to squeeze onto the eye shield and eyelids with the requisite pressure without putting pressure on the eye orbital.

As shown in the figures, the eye shield 80 is positioned at a front end of the massage apparatus 20, where the subject's eye is engaged, in order to position the massage tips 70 in the proper relative position during use of the apparatus 20. Once the eye shield 80 is installed on the patient's eye, the handheld unit is maneuvered to position the quick-release mechanism 98 at the eye shield tab 86. The treatment lever 30 is then manipulated to capture the eye shield tab 86 in the quick-release mechanism 98 and move the massage arms 50 forward to the extended position, which allows the massage tips 70 to engage the eyelids with a massaging motion when the apparatus 20 is operated.

Figure 13:
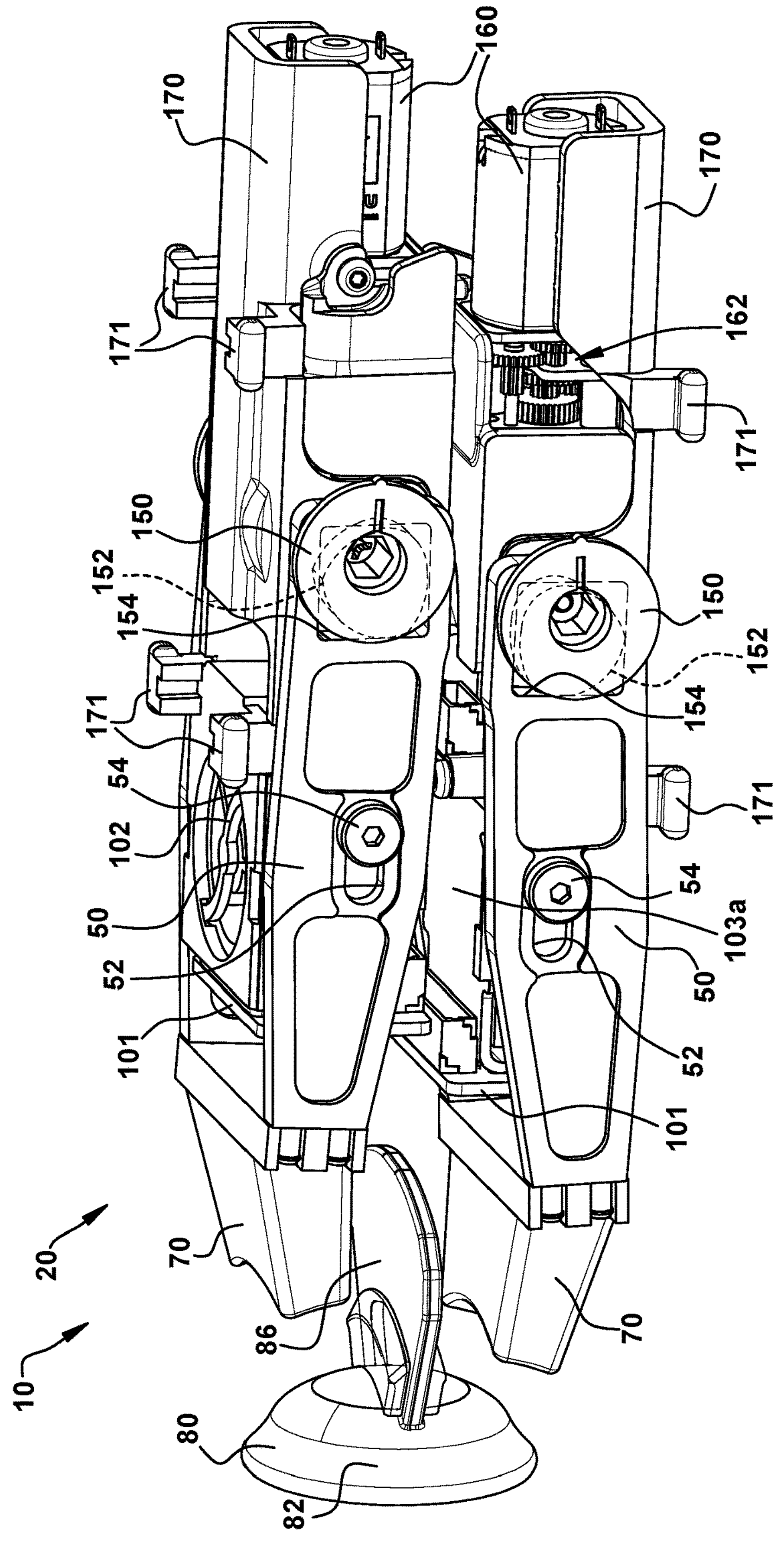
FIG. 13 is a side perspective view of certain components of the apparatus.
Figure 20:
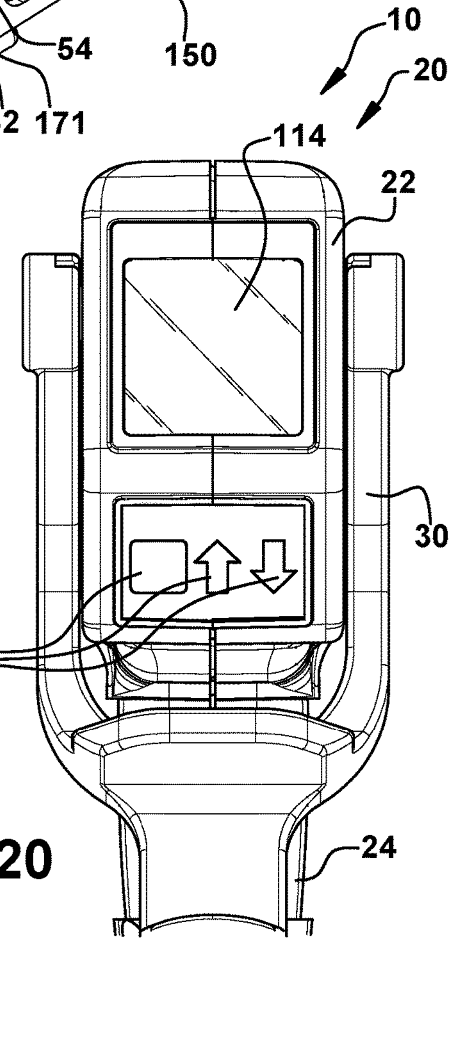
FIG. 20 is a rear view of the apparatus.

On top of the housing 22, IR heating controls 110 allow the doctor using the apparatus to control the heat settings for IR heat applied via the LED array 100 as well as cooling provided by cooling fans 102, both of which are supported by and between the upper and lower pairs of massage arms 50. Excess resistive heat is transferred from the backside of the PCBA 101 to the fans 102 via a metal heat spreader connected to fins 103 (FIG. 13). As shown in FIG. 20, at the rear of the housing 22, power/massage controls 112 allow the ophthalmologist to power on the apparatus and can optionally have up and down arrows to adjust setting parameters like pressure, temperature, or treatment time before treatment starts.

A rear-mounted display 114 approximately 1" or more in width can be used to indicate several metrics such as the time left in the treatment, battery level remaining, which eye and eyelid are being treated as well as current eyelid treatment temperatures. In addition, a wireless video connection can be used to project a large display of the MGD treatment during the process using internal micro cameras 104 (see FIG. 16), such as wafer-scale micro cameras from OmniVision Technologies, Inc. or others. In one example, the cameras 104 can be mounted on the same PCBA 101 as the LED array 100 (see, e.g., FIGS. 17-19).

The massage carriage 170 and arms 50 support several components that facilitate the application of heat and massaging motion while monitoring the progress of the therapy via the video screen. The LED arrays 100 and their associated cooling fans 102 are mounted at the rear of the massage tips 70. These tips 70 are constructed of a material, such as silicone or polyurethane, that allows IR energy to pass through their structures and heat the eyelids. The IR energy can therefore be applied directly to the eyelids at the precise location where the massage therapy is applied. In fact, the massage tips 70 can be configured to guide and/or focus the IR energy on specific portions of the eyelid so that the meibomian gland and the obstruction(s) of the gland orifice (s) can be heated, both before and during massage treatment. The LED arrays 100 can be stationary relative to the massage arms 50, but the motion of the massage arms/massage tips is still small enough that the light from the LED array is funneled through the massage tips.

The micro cameras 104 of the massage carriage 170 can be mounted directly to the PCBA 101 and therefore do not move along with the massage arms/tips. In one example configuration, the cameras 104 can be directed toward angled mirrors 87 internal to the optical insert 88 that directly capture scattered IR light from the eyelid margin back to the micro cameras 104 by imaging through the transparent insert 88. The chief central ray 74 is shown as a dotted line in FIG. 16 for each camera. This allows the doctor to view the progress of the therapy in real time via the rear mounted screen or, more easily, via a large external display. Alternatively, the micro cameras 104 could potentially be mounted somewhere else in a different location to focus directly on the eyelids.

Figure 19:
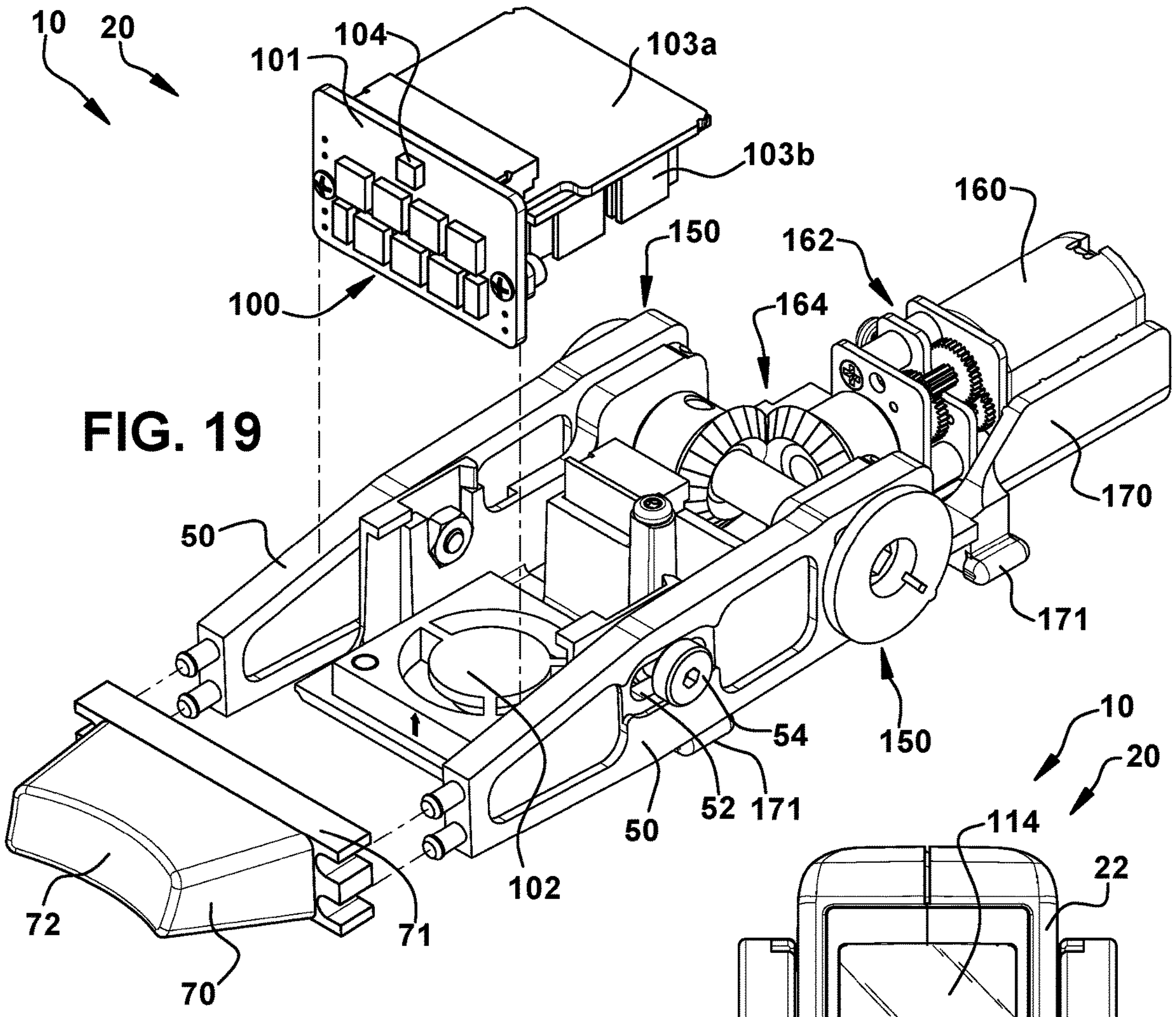
FIG. 19 is an exploded perspective view of one of the components of FIG. 17.

The massage apparatus 20 includes a sliding massage carriage 170 holding the massage arms 50 which can be driven by motor 160 and gears 162 into a "milking motion" relative to the position of the ridge carriage 170. There are two massage carriages 170, one associated with each pair of massage arms 50, i.e., one associated with the upper massage arms, and one associated with the lower massage arms. The massage carriage 170 is fixed relative to the massage arms 50. The massage carriage 170 can slide forward or backward, i.e. towards or away from the eye shield using gliding feet 171 that slide inside a guiding rail 172 in the housing (FIG. 21) As best shown in FIGS. 13 and 19, each massage carriage 170 supports drivetrain components including a motor 160 for producing rotational motion, a speed reducing gear mechanism 162, and a gear mechanism 164, such as a miter gear, for translating the axis of rotation of the motor and speed reducing gear mechanism along a different shaft direction. The drivetrain components and the manner in which the drivetrain components impart rotational movement to the massage apparatus 20 is not particularly important, and alternative mechanisms, components, etc. can be implemented. Additionally, instead of individual sets of drivetrain components for each pair of massage arms 50, the apparatus 20 could include a single set of drivetrain components configured to impart movement of both pairs, upper and lower, of massage arms.

Each pair of massage arms 50 (upper and lower) supports a massage tip 70. The massage tips 70 are configured, at least partially, to include soft portions or pads 72 that physically engage the eyelids. The massage tips 70 can be formed of a soft IR transparent material, such as silicone rubber, that is compliant and suitable for direct engagement with eyelid skin/tissue. The massage tips 70 can be formed of a single piece of homogeneous material so that the pads 72 are integral to the massage tips. Alternatively, the pads 72 can be constructed of a material, such as silicone rubber, and attached to a more rigid material at the base 71, which can be secured to the massage arms 50 via pin connections (see, FIGS. 18-19). The massage pads 72 can have a shape on the eyelid contact side 72 configured to mimic and conform to the customary anatomy of the average eyelid and be soft enough to conform to any shape.

The motion imparted to the massage arms 50 by the drivetrains 170 is described with reference to FIG. 14, which is a schematic representation of a massage arm. The massage arm 50 extends along a longitudinal axis, referred to herein as $A_T$, because it is this axis along which translational movement of the massage arm takes place, as indicated generally by the arrow labeled L in FIG. 14. The massage arm 50 is supported by a pin/slot mechanism formed by the fixed pin 54 and the elongated slot 52 in the massage arm though which the pin extends. The pin 54 defines a pivot axis $A_P$ about which the massage arm 50 can pivot or rotate, as indicated generally by the arrow labeled P in FIG. 14. The slot 52 is configured to extend along the length of the massage arm 50, i.e., along the axis $A_T$. The motion of the massage arm 50 imparted by the drivetrain 170 can thus be linear motion L along the axis $A_T$, pivotal motion about the pivot axis $A_P$, or a combination of linear and pivotal motion.

The massage apparatus 20 also includes a cam/follower mechanism 150 configured to translate the rotational motion imparted by the drivetrain 170 to linear and pivotal movement of the massage arms 50. The cam/follower mechanism 150 is illustrated schematically in FIG. 14. As shown in FIG. 14, massage arm 50 is configured to slide back and forth via the pin/slot slider mechanism linearly along the linear axis $A_T$, as indicated generally by the arrow L, and to pivot via the pin/slot slider mechanism about the pivot axis $A_P$, as indicated generally by the arrow P. The cam/follower mechanism 150 includes a cam 152 positioned in a follower 154. As shown in FIG. 14, the follower 154 can be an opening extending into/through the massage arm 50.

The cam 152 has a rounded polygonal configuration with a cam surface 156 that forms a curve of constant width, similar to a Reuleaux triangle. The follower 154 has a square configuration with a square follower surface 158 having a width about equal to the width of the constant curve of the cam 152. The cam 152 thus fits within the follower 154 and can rotate within the follower, with the cam surface 156 maintaining a constant engagement with the follower surface 158. The materials used to construct the cam 152 and the follower 154 can be selected to promote a sliding engagement between the cam and follower surfaces 156, 158 with minimal friction and minimal wear. The cam/follower material can, for example, be a plastic Delrin® acetal homopolymer (Polyoxymethylene POM), which is available commercially from Dupont de Nemours, Inc., or similar material with natural dry lubrication. Lubricants, such as grease, can also be additionally used.

Figure 14:
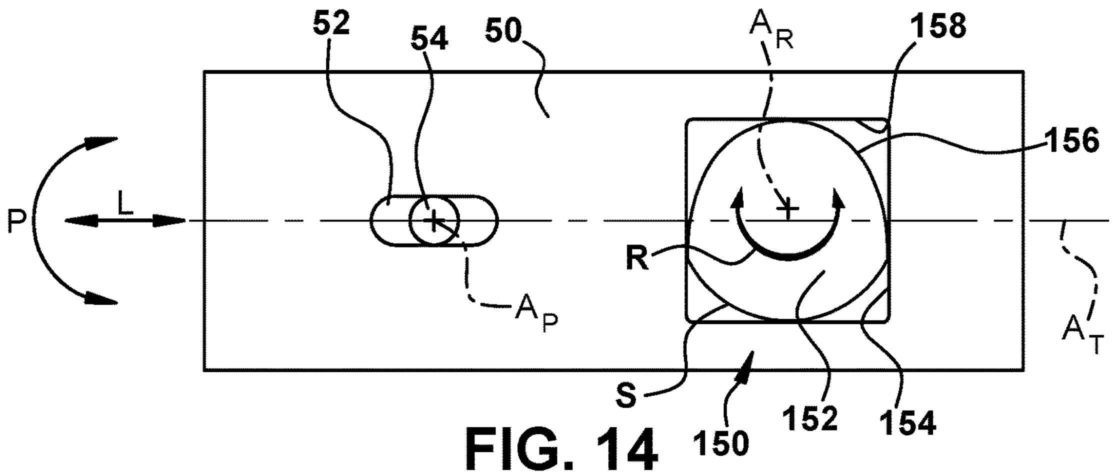
FIG. 14 is a schematic illustration depicting the operation of some of the components of FIG. 13.

The cam 152 is rotatable about a rotational axis $A_R$, as indicated generally by the arrow labeled R in FIG. 14. The rotational axis $A_R$ of the cam 152 is offset from its center so as to produce an eccentric motion when rotated. Because the cam surface 156 is configured to maintain engagement with all four sides of the follower surface 158, the cam 152 acts as a positive return cam. The eccentric rotational motion of the cam 152 imparts motion to the massage arm 50, and that motion can be linear (arrow L), pivotal (arrow P) or a combination of linear and pivotal.

The motion of the massage arm 50 produced by the cam/follower mechanism 150 is configured to produce a desired massaging motion at the massage tip 70 of the massage arm 50. Advantageously, the massaging motion is rectangular in form. The characteristics of the massaging motion can be controlled through the configuration/adjustment of the following parameters, individually or in combination:

The size and/or constant-curve shape/width of the cam 152.

The offset distance between the center of the cam and the center of rotation $A_R$.

The distance of the pin/slot slider mechanism 52, 54 from the center of rotation $A_R$.

The length of the massage arm 50.

By configuring/adjusting these parameter(s), a wide variety of rectangular shapes for the massage tip path can be achieved.

Figure 15:
FIG. 15 is a table illustrating the operation of the components of FIG. 14.
Figure 15:
Figure 15:
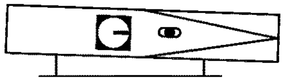
Figure 15:
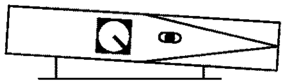
Figure 15:
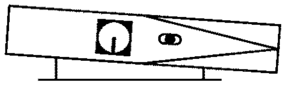
Figure 15:
Figure 15:
Figure 15:
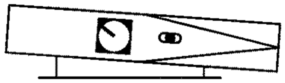

In an example configuration, the massage assembly can be configured to produce a rectangular path at the massage tip, with linear back and forth movement, towards and away from the eyelids, of 1 mm and a pivotal up and down squeeze motion of between 1 and 2 mm. This action produces the rectangular motion of the massage pads, which engage and massage the eyelid to treat MGD. This motion is shown in FIG. 15, which shows a sequential series of figures that show the state of the massage apparatus at various rotational angles of the cam 152. In these figures, the cam 152 rotates clockwise. Linear left/right movements are designated with negative value for left/down and positive values for as right/up.

From the 0° position, the cam rotates counterclockwise, as shown by the line indicator on the cam 152 through the positions shown in the table. Due to the offset of the rotational axis $A_R$, a portion of the cam surface 156 opposite the rotational axis $A_R$, surface S, imparts the motion to the massage arm. Because cam surface S is circular in form, the movements imparted by cam surface S is constant through its engagement with any of the four sides of the follower surface 158. This produces distinct linear/pivotal movements of the massage arm 50, which translates to corresponding distinct movements of the massage tip 70, throughout specific angular ranges of cam rotation, which are shown in FIG. 15.

In the example of FIG. 15, pivotal tip movement is defined by the configuration of the massage assembly to be 2.0 mm, with +1.0 mm being the up position, and −1.0 mm being the down position. Linear tip movement is defined by the configuration of the massage assembly to be 1.0 mm with +0.5 mm being the tip left position, and −0.5 mm being the tip right position.

As shown in FIG. 15, at the 0° cam position, the massage tip is at a Center 0 mm position linearly with the tip pivoted +1.0 mm Up. As the cam rotates (clockwise in the example) to the 45° position, the tip moves to the Left −0.5 mm position and is maintained at the Up position. As the cam rotates to the 90° position, the tip is maintained at the Left position and moves to the −1.0 mm Down position. As the cam rotates to the 135° position, the tip is maintained at the Left position and the Down position. As the cam rotates to the 180° position, the tip moves to the Center position and is maintained at the Down position. As the cam rotates to the 225° position, the tip moves to the +0.5 Right position and is maintained at the Down position. As the cam rotates to the 270° position, the tip is maintained at the Right position and moves to the Up position. As the cam rotates to the 315° position, the tip is maintained at the Right position and the Up position. The cycle then repeats at the 0° position.

In practice, the motion of the massage arms 50 described above is advantageous in treating a subject with MGD. This is illustrated schematically in FIG. 16, which is a close-up illustration of the massage apparatus positioned to treat a subject with MGD. As shown, the massage apparatus 20 is positioned relative to the eye with the eye shield 80 positioned on the eyeball. In this condition, the eye shield 80 serves the dual purpose of controlling the position of the massage arms relative to the eye and the eyelids while, at the same time, shielding the eye from IR radiation emanating from the LED array 100. For added safety, the eye shield can include temperature sensors configured to control the LED array 100 to maintain a desired temperature or to turn off the LED array if the temperature becomes too high.

The relative position of the eye shield to the massage arms can be fine-tuned so that a desired amount of pressure is exerted on the eyelids during the massage session. It may, for example, be desirable to massage the eyelids with a pressure of 2 psi. For this purpose, the apparatus 20 can be configured to fine-tune the positions of the massage arms 50 relative to the eye shield 80 which, in effect, controls the positions of the massage tips 70 relative to the patient's eyelids. This is important because the anatomy of every patient differs, so the distance of the massage tips 70 from the eye shield 80 necessary cause the desired pressure to be applied will vary from patient to patient. This fine-tuning helps control precisely the pressure applied to the patient's eyelids by the massage arms 50 via the massage tips 70.

Figure 21:
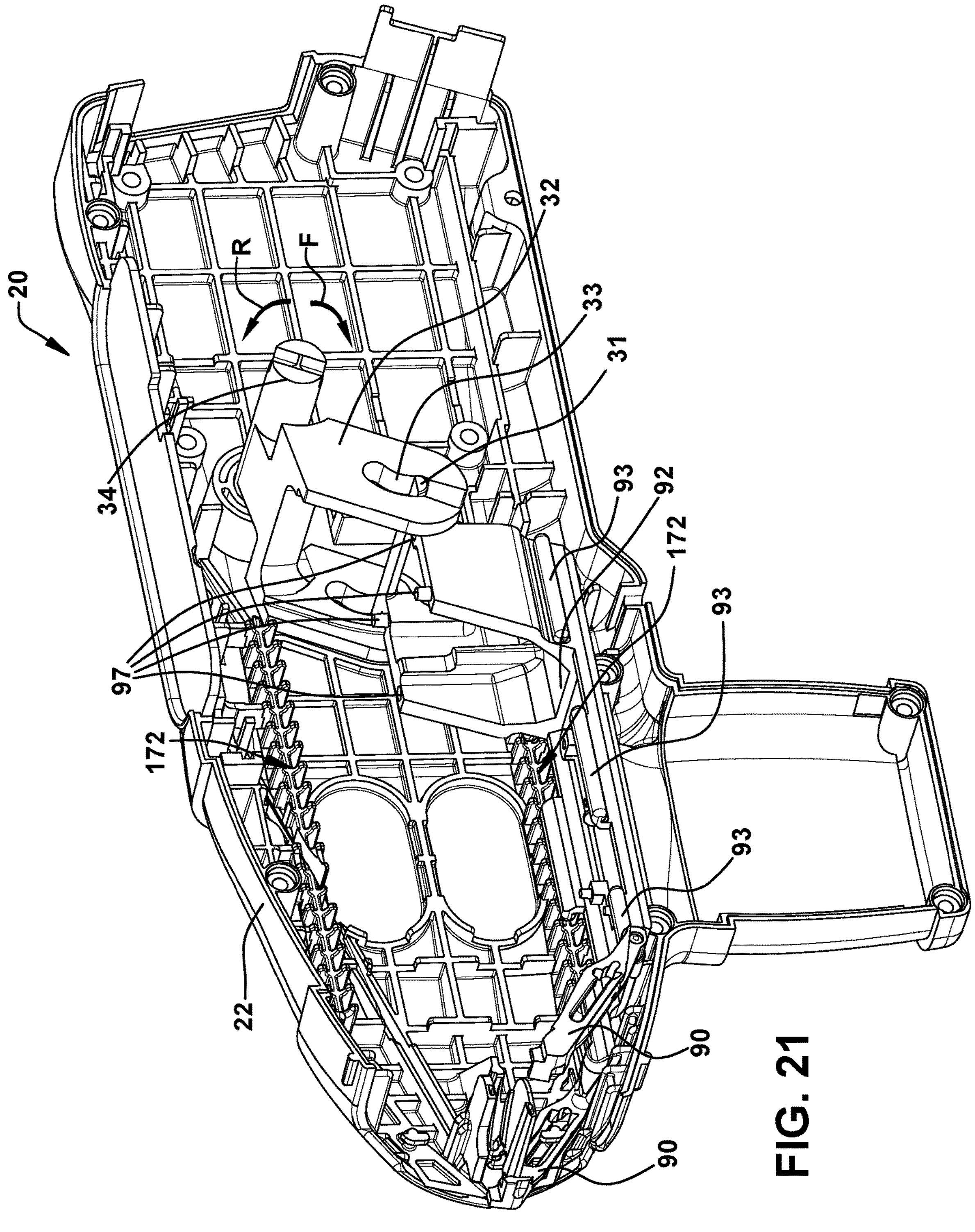
FIGS. 21 and 22 are magnified perspective views with portions removed so as to illustrate certain components of the apparatus.
Figure 22:
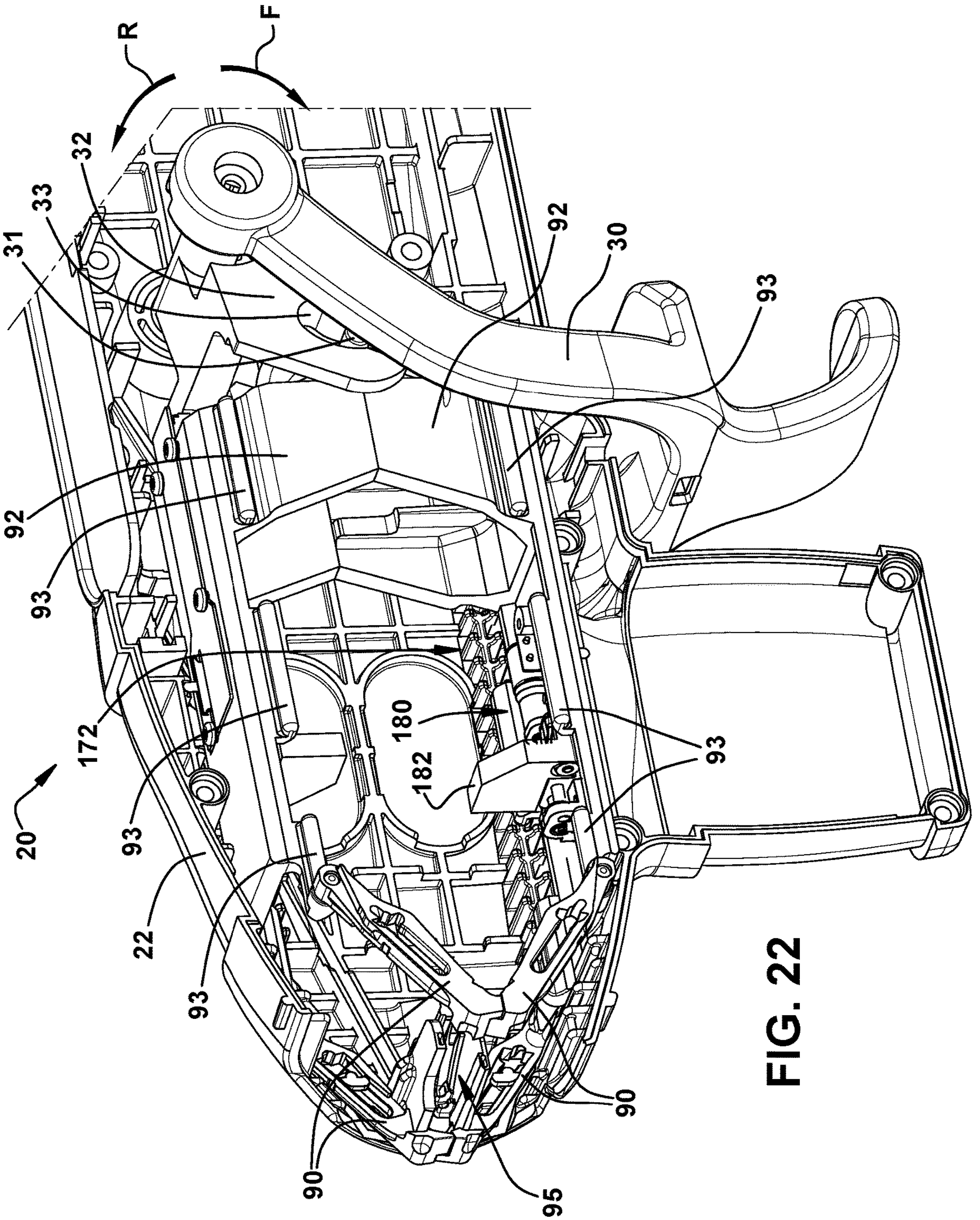

The forward motion of the massage tips 70 can be precisely adjusted to achieve a precise pressure on the eyelids via the forward motion carriage 92, which interfaces with the massage carriages 170. Referring to FIGS. 21 and 22, the forward motion carriage 92 includes upper and lower halves that are interconnected via mating pins/holes 97 so that the forward motion carriage 92 slides in the housing 22 along the guide rail 172 via the feet 93 as a unit. The massage carriages 170 are separate and individually slidable along the guide rail 172 via their respective feet 171. The massage carriages 170, carrying the massage arms 50 and their respective drivetrain components, are movable, individually, relative to the forward motion carriage 92.

The forward motion carriage 92 includes a pin 31 that interfaces with a slot 33 of an internal lever 32 that is actuatable via the treatment lever 30 to pivot relative to the housing 22 about a shaft 34. Forward actuation of the treatment lever 30 causes forward rotation (arrow F) of the internal lever 32. Rearward actuation of the treatment lever 30 causes rearward rotation (arrow R) of the internal lever 32. Through engagement of the pin 31 in the slot 33, forward rotation of the internal lever 32 moves the forward motion carriage 92 and the massage carriages 170 forward along the guiderail 172. Rearward rotation of the internal lever 32 moves the forward motion carriage 92 and the massage carriages 170 rearward along the guiderail 172. Thus, the treatment lever 30, when actuated to the forward position, moves the forward motion carriage 92 and the massage carriages 170 to the forward, extended position (see, e.g., FIGS. 5, 8, 11, 21, and 22). Similarly, the treatment lever 30, when actuated to the rearward position (e.g., via the torsion springs 99 when released) moves the forward motion carriage 92 and the massage carriages 170 to the rearward, retracted position (see, e.g., FIGS. 3, 4, 6, and 7).

Figure 23:
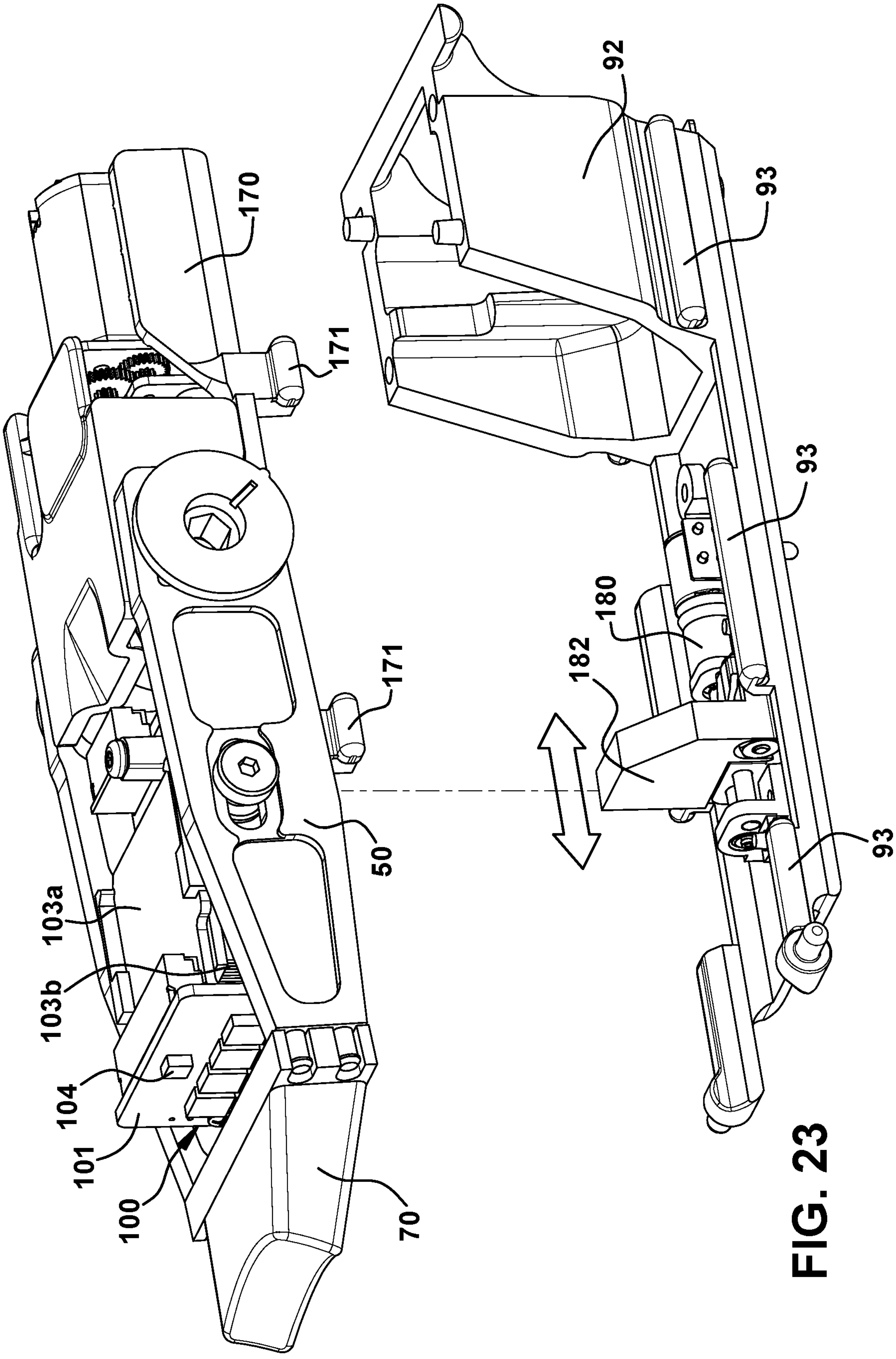
FIG. 23 is an exploded perspective view with portions removed so as to illustrate certain components of the apparatus.
Figure 24:
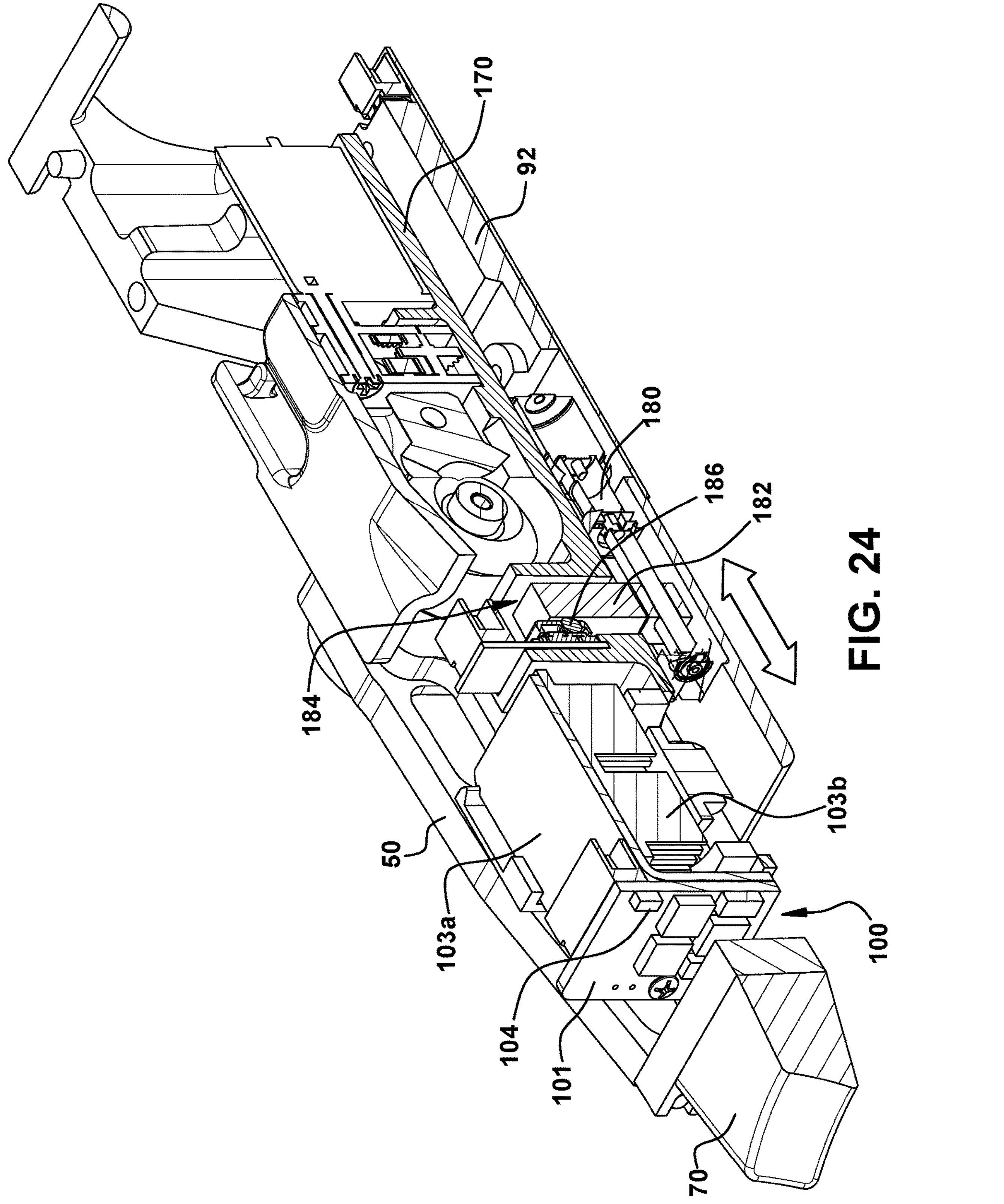
FIG. 24 is a perspective sectional view of the components of FIG. 23 in an assembled condition.
Figure 25:
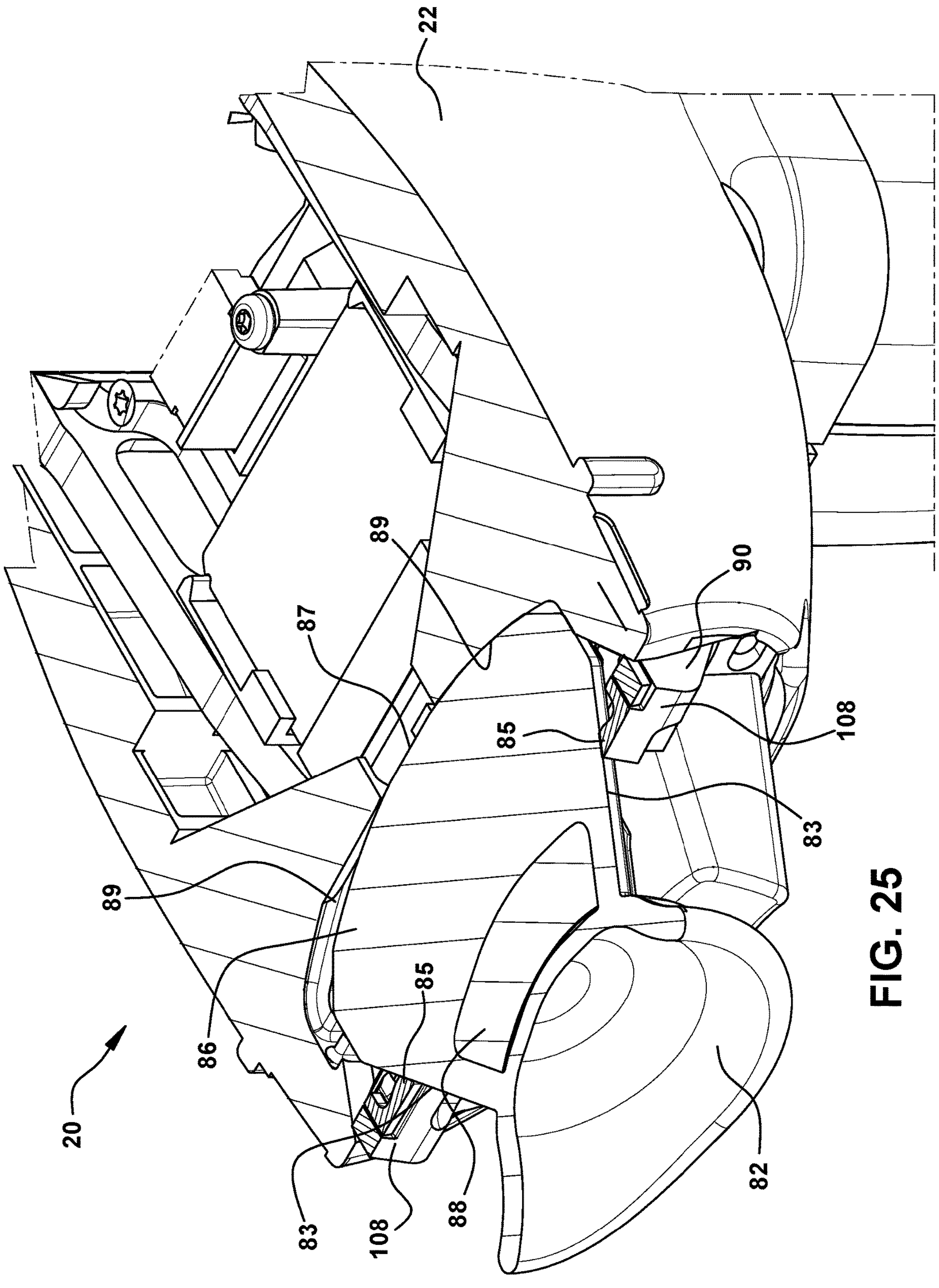
FIG. 25 is a magnified perspective section view illustrating the fit of certain components of the apparatus in an assembled condition.

Referring to FIGS. 23 and 24, the forward motion carriage 92 carries stepper motors 180 configured to individually bias the massage carriages 170 forward and rearward relative to forward motion carriage in order to effectuate an individual, fine-tuned adjustment of the massage arms 50 relative to the housing 22, the eye piece 80, and the patient's eyelids. While FIGS. 23 and 24 illustrate the lower half of the forward motion carriage 92 and its associated massage carriage 170, massage arm 50, and other components, it will be appreciated that the upper half of the forward motion carriage and its associated components are configured and operate in an identical manner.

The stepper motor 180 is operable to move an associated drive block 182 forward and rearward along the forward motion carriage 92. As shown in FIG. 24, the drive block 182 is received in a slot or channel 184 in the massage carriage 170, so that the drive block moves the massage forward and rearward with respect to the forward motion carriage. A force sensor 186 is located inside the channel 184. When the stepper motor 180 moves the drive block 182 forward, it engages the force sensor 186 and exerts the movement force on the force sensor attached to carriage 170. Forward movement of the massage carriage 170 is therefore transmitted from the forward motion of carriage 92 through the force sensor 186. The force sensor 186 can be configured from firmware to halt the fine-tuning imparted by the stepper motor when a predetermined force level is sensed due to the back action compression of the massage tip. This level can be calibrated to a given pressure squeezing the eyelid and massage tip by performing verification and validation testing. Thus, when fine-tuning the positions of the massage arms 50 via operation of the stepper motor in situ with the eye piece 80 latched into the apparatus 20 and installed in the patient's eye, the stepper motor 180 can adjust the position of the massage tips 70 until the desired pressure (e.g., 2 psi) is reached. This fine-tuning can be done individually for each eyelid, upper and lower, so that the apparatus 20 can be fine-tuned to the patient's anatomy.

Once the apparatus 20 is fine-tuned to apply the desired pressure to the eyelids, the apparatus can be operated to apply massage motion to the eyelids. The massage motion can be described loosely as a "milking" motion, because it is configured to squeeze the meibomian glands and apply massage motion in a singular expelling direction, to release the squeeze and return to the starting point, where the squeeze is re-applied and the massage motion is repeated.

In the example configuration disclosed herein, the milking massage motion is a square massage motion, which is indicated generally by the square arrows in FIG. 16. The massage motion follows that set forth in the sequence illustrated in the table of FIG. 15. Noting that the motion is different, i.e., opposite, for the upper eyelid and the lower eyelid, the motion laid out in FIG. 15 is that of the massage arm for the lower eyelid. The motion for the upper eyelid is opposite that of the lower eyelid and can be interpolated from FIG. 15. The upper and lower motions can be achieved simply by flipping the massage carriages 170 and the components supported therein upside-down. This rotational symmetry has the effect of rotating the cam in opposite directions, e.g., clockwise for the lower eyelid and counterclockwise for the upper eyelid. Thus, both the upper and lower massage carriages 170, and the respective components supported therein, can be built with the same motor connections and same intrinsic specs, which means there is no need for different upper and lower 172 slider inventory management.

Figure 17:
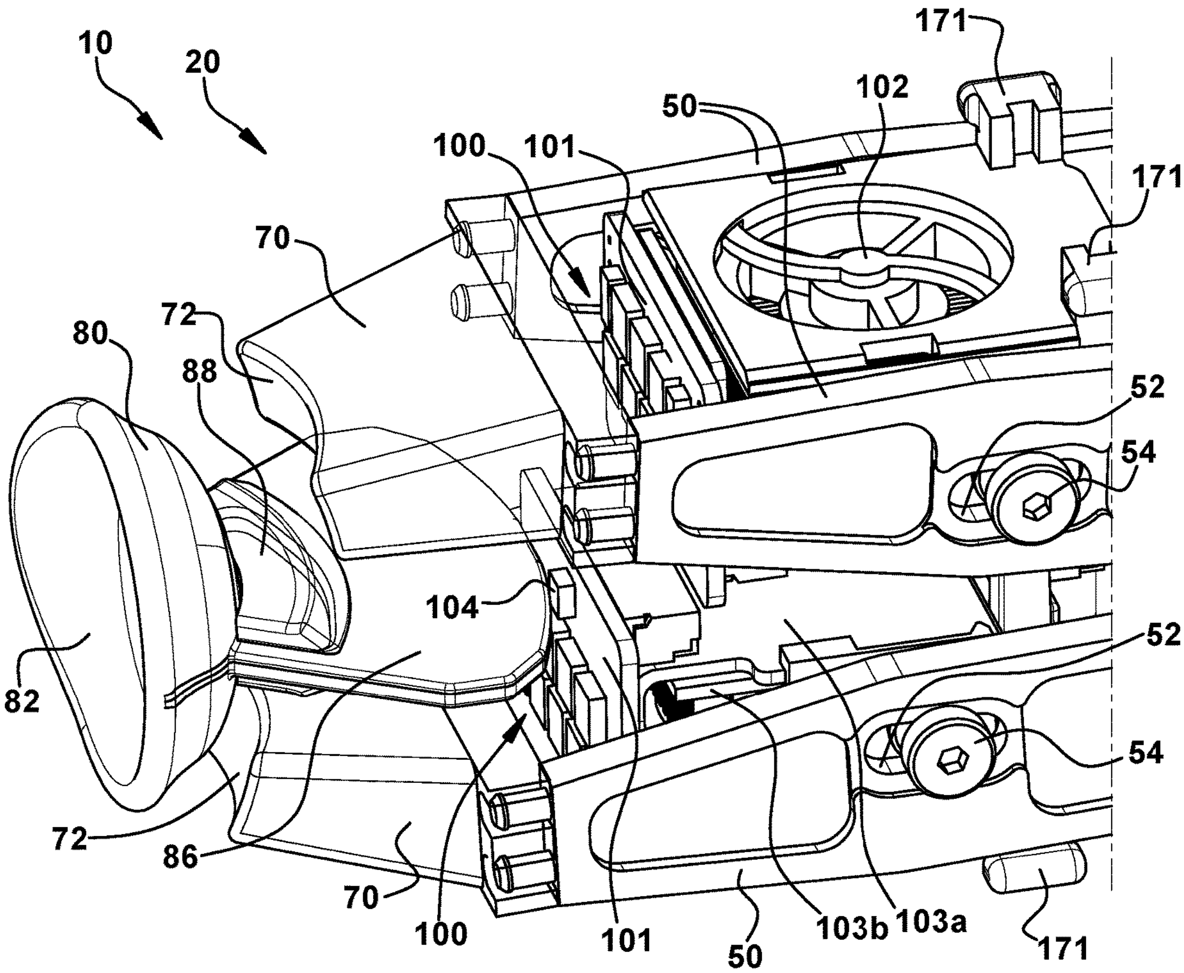
FIG. 17 is a magnified perspective view of the components of FIG. 16.
Figure 18:
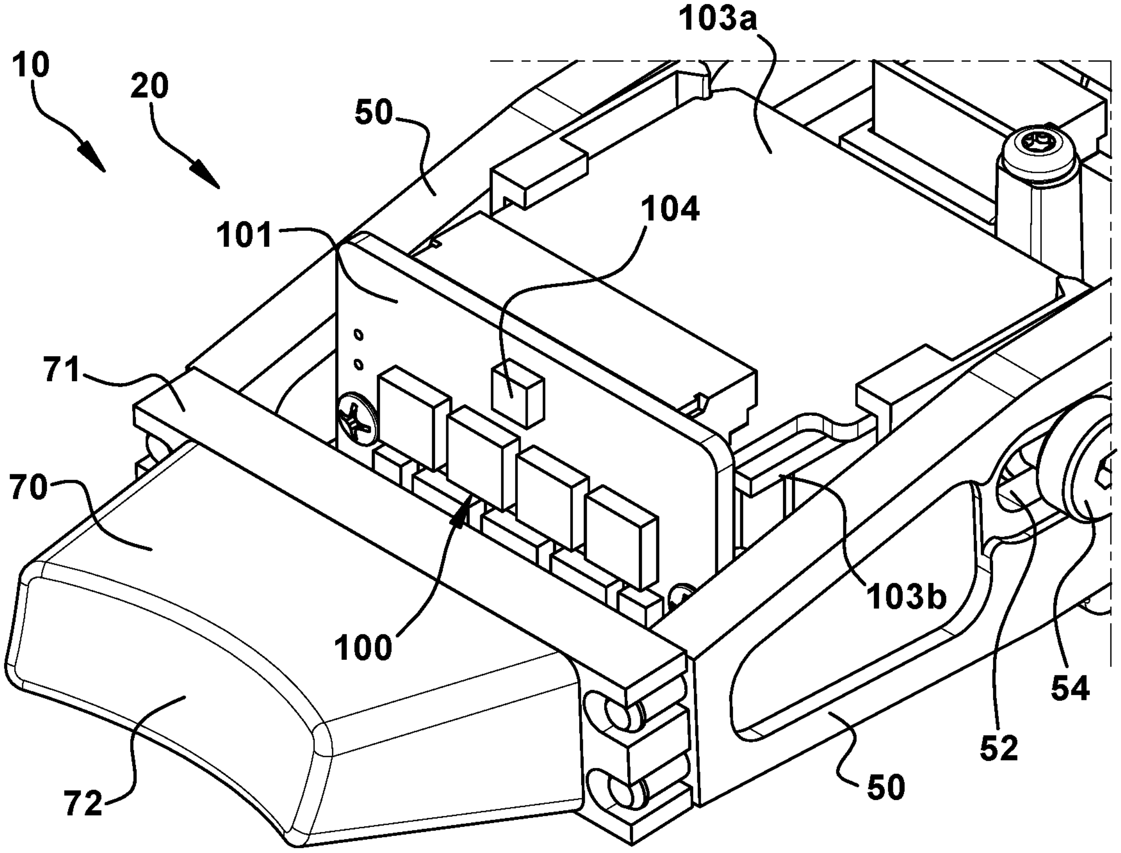
FIG. 18 is a perspective view of one of the components of FIG. 17 magnified further.

Referring to FIG. 16, and with reference to FIGS. 17-19, the LED array 100 can be arranged to direct light straight through the transparent massage tips 70, which can, for example, be constructed of silicone or polyurethane. In one example configuration, the LED array 100 can be arranged in one or more parallel rows oriented to project light straight through the massage tips 70, as shown.

At the same time that the massage motion is being applied to the eyelids, the orifices of the meibomian glands, can be heated via the LED array 100. This heating lowers the viscosity of the meibum in the glands, which promotes unclogging meibum flow in response to the massage motion applied via the massage arms 50. As indicated in FIG. 16, the upper massage arm 50 moves in a square motion in the following order: left, down, right, up. Similarly, the lower massage arm moves in an opposite square motion in the following order: right, down, left, up. Through these motions, the massaging effect on the eyelids and, particularly, the meibomian glands, is the cyclical application of pressure that is akin to a milking motion of squeezing the eyelid/gland and then moving in the direction of the gland orifice to expel the clog and move the meibum, followed by releasing the squeeze and returning to the initial position so that the motion can be repeated.

From the above description, those skilled in the art will perceive improvements, changes, and modifications. These and other such improvements, changes and modifications within the skill of the art are intended to be covered by the appended claims.

We claim:

1. An apparatus configured to massage an eyelid to move meibum unidirectionally through a meibomian gland duct toward a meibomian gland duct orifice at an eyelid margin in order to clear meibum blockage in the meibomian gland duct, the apparatus being configured to cyclically apply pressure to an application area of the eyelid, to move the applied pressure in a flow direction toward the meibomian gland duct orifice, and release the pressure applied to the application area of the eyelid, the apparatus comprising:

an elongated massage arm configured to support a massage tip, the massage tip being configured to apply the pressure to the application area of the eyelid;

a cam rotatable about an axis of rotation, the cam comprising a cam surface; and a follower comprising an opening in the elongated massage arm defining a follower surface in sliding engagement with the cam surface, wherein the opening has a generally square shape;

wherein the follower is configured to impart a massaging motion to the elongated massage arm in response to rotation of the cam;

wherein the cam has a rounded polygonal configuration and the cam surface has a constant width curve configuration;

wherein the cam is configured so that a center of the cam surface is offset from the axis of rotation of the cam, wherein the cam and the follower are configured so that the massaging motion follows a rectangular path, wherein the rectangular path is configured sequentially to be axially toward the eyelid into engagement with the application area, linearly along the eyelid in the flow direction of the meibomian gland duct while engaged with the application area, axially away from the eyelid to disengage from the application area, and linearly in a direction opposite the flow direction while disengaged from the application area.

2. The apparatus recited in claim 1, wherein the cam and the follower are configured so that the massaging motion of the massaging comprises the following movements in a repeating cycle:

a first movement comprising moving from an initial position into engagement with and applying pressure to the application area of the eyelid;

a second movement comprising moving in the flow direction toward the meibomian gland duct orifice while applying pressure to the application area;

a third movement comprising moving away and disengaging from the eyelid; and a fourth movement comprising returning to the initial position.

3. The apparatus recited in claim 1, wherein the follower surface comprises a surface of the elongated massage arm.

4. The apparatus recited in claim 1, wherein the cam is positioned in the opening, the opening having a width greater than a width of the constant width curve of the cam surface, the width of the opening being configured to allow the cam to rotate within the opening while engaging the follower surface.

5. The apparatus recited in claim 1, wherein the cam is configured so that the cam surface is maintained in constant contact with all four sides of the square opening of the follower.

6. The apparatus recited in claim 1, further comprising a pin/slot mechanism that supports the elongated massage arm on the housing, the pin/slot mechanism comprising a fixed pin supported on the housing and a slot on the elongated massage arm through which the pin extends, wherein the elongated massage arm is configured to pivot about the fixed pin and to slide on the fixed pin along the length of the slot.

7. The apparatus recited in claim 1, wherein the cam and follower are configured so that rotational motion of the cam produces a rectangular motion of the massage tip.

8. The apparatus of claim 1, further comprising at least one source of infrared light configured to heat the meibum in the eyelid meibomian gland ducts through the massage tip either independently from the massage motion of the massage tip or simultaneously with the motion of the massage tips.

9. The apparatus of claim 8, wherein the infrared light is emitted at a wavelength of about 900 nm to 1100 nm, preferably at a wavelength of about 985 nm to 1015 nm.

10. The apparatus of claim 8, further comprising an eye shield configured to engage and cover at least a portion of the eye and to be positioned between the eye and the eyelid to shield the eye from the infrared light.

11. The apparatus of claim 10, wherein the eye shield comprises a translucent portion through which visible can pass, the translucent portion being configured to allow for a camera to image the eyelids during treatment.

12. The apparatus of claim 9, wherein the massage tip is configured to allow infrared radiation to pass through and apply heat to the eyelid.

13. The apparatus of claim 10, further comprising latching arms with latching tips configured to move toward each other to a latching condition in which the latching tips latch a tab portion of the eye shield to secure the eye shield to the apparatus and constrain movement of the eye shield relative to the elongated massage arm.

14. The apparatus of claim 13, wherein the apparatus comprises a treatment arm that is actuatable from a retracted position to a treatment position, wherein the treatment arm is configured to move the latching arms to the latching condition when in the treatment position, and to move the latching arms to the release condition when in the retracted position, wherein the treatment arms include a spring member configured to bias the treatment arm to the retracted condition when released so that a quick-release of the eye shield tab portion is effectuated automatically.

15. The apparatus of claim 14, wherein the treatment arm is also configured to control actuation of a forward positioning carriage that carries the elongated massage arm, the treatment arm being configured to move the forward positioning carriage linearly to position the elongated massage arm in a retracted condition when not applying massage motion, and an extended position for applying massage motion to the eyelids.

16. The apparatus of claim 1, further comprising an LED array arranged to provide light for optical heating, the LED array being configured for adjustment in brightness to provide high contrast imaging light for video imaging of the meibomian glands for a brief period during heating.

17. The apparatus of claim 16, wherein the LED heating array is supported on a PCBA, and wherein the PCBA also supports mounting of a micro camera.

18. The apparatus of claim 17, wherein the eye shield further comprises a transparent portion that includes one or more embedded mirror surfaces, the mirror surfaces being configured to allow the micro camera to view the eyelid and meibomian gland duct orifices edge-on by redirection of the chief collection rays of the micro camera towards the upper and lower eyelid margins.

19. The apparatus of claim 16, further comprising a fan and a heatsink for cooling the LED array.

20. The apparatus of claim 1, wherein the cyclically applied pressure is configured to be 8 psi or less.

* * * * *